(12) United States Patent
Cao et al.

(10) Patent No.: US 7,819,868 B2
(45) Date of Patent: Oct. 26, 2010

(54) ABLATION CATHETER WITH FLUID DISTRIBUTION STRUCTURES

(75) Inventors: Hong Cao, Savage, MN (US); Chou Thao, Brooklyn Center, MN (US); Kedar R. Belhe, Minnetonka, MN (US); Saurav Paul, Minneapolis, MN (US); Todd Stangenes, Minneapolis, MN (US)

(73) Assignee: St. Jude Medical, Atrial Fibrilation Division, Inc., St. Paul, MN (US)

( * ) Notice: Subject to any disclaimer, the term of this patent is extended or adjusted under 35 U.S.C. 154(b) by 958 days.

(21) Appl. No.: 11/158,944

(22) Filed: Jun. 21, 2005

(65) Prior Publication Data
US 2006/0287650 A1    Dec. 21, 2006

(51) Int. Cl.
*A61B 18/14*    (2006.01)

(52) U.S. Cl. .............................................. 606/41

(58) Field of Classification Search ............... 606/41, 606/45, 46, 48–50; 607/101–105
See application file for complete search history.

(56) References Cited

U.S. PATENT DOCUMENTS

| | | | |
|---|---|---|---|
| 4,641,649 A | 2/1987 | Walinsky et al. | |
| 4,776,334 A | 10/1988 | Prionas | |
| 4,860,769 A | 8/1989 | Fogarty et al. | |
| 4,896,671 A | 1/1990 | Cunningham et al. | |
| 4,934,049 A | 6/1990 | Kiekhafer et al. | |
| 4,945,912 A | 8/1990 | Langberg | |
| 4,976,711 A | 12/1990 | Parins et al. | |
| 5,125,895 A | 6/1992 | Buchbinder et al. | |
| 5,125,896 A | 6/1992 | Hojeibane | |
| 5,178,618 A * | 1/1993 | Kandarpa | 606/28 |
| 5,209,229 A | 5/1993 | Gilli | |
| 5,228,442 A | 7/1993 | Imran | |
| 5,231,995 A | 8/1993 | Desai | |
| 5,239,999 A | 8/1993 | Imran | |
| 5,242,441 A | 9/1993 | Avitall | |
| 5,246,438 A | 9/1993 | Langberg | |
| 5,255,679 A | 10/1993 | Imran | |

(Continued)

FOREIGN PATENT DOCUMENTS

WO    WO 95/10319    4/1995

OTHER PUBLICATIONS

PCT International Search Report and Written Opinion of the International Searching Authority for PCT/US06/23854, dated Oct. 30, 2007, 8 pages.

*Primary Examiner*—Lee S Cohen
(74) *Attorney, Agent, or Firm*—Trenner Law Firm LLC

(57) ABSTRACT

An ablation catheter has improved fluid distribution structures. An ablation section at a distal end of the catheter is designed to provide a more uniform fluid flow emanating from the catheter. By creating a uniform fluid flow, a more uniform tissue lesion results and the possibility of charring the tissue is reduced. A combination of mesh material layers, porous materials, and dispersion channels or openings are used to achieve the uniform flow. The amount of fluid used as a virtual electrode to ablate the tissue is greatly reduced with the present invention. Further, the catheter may be used to create a single, uniform linear lesion by successive application of energy to adjacent portions of the ablation section, thus reducing the power required to create the desired lesion.

20 Claims, 12 Drawing Sheets

U.S. PATENT DOCUMENTS

| | | | |
|---|---|---|---|
| 5,263,493 A | 11/1993 | Avitall | |
| 5,269,757 A | 12/1993 | Fagan et al. | |
| RE34,502 E | 1/1994 | Webster, Jr. | |
| 5,277,199 A | 1/1994 | DuBois et al. | |
| 5,279,299 A | 1/1994 | Imran | |
| 5,281,213 A | 1/1994 | Milder et al. | 606/15 |
| 5,281,217 A | 1/1994 | Edwards et al. | 606/41 |
| 5,293,868 A | 3/1994 | Nardella | |
| 5,311,866 A | 5/1994 | Kagan et al. | |
| 5,318,525 A | 6/1994 | West et al. | |
| 5,324,284 A | 6/1994 | Imran | |
| 5,327,889 A | 7/1994 | Imran | |
| 5,327,905 A | 7/1994 | Avitall | |
| 5,330,466 A | 7/1994 | Imran | |
| 5,334,193 A | 8/1994 | Nardella | 606/41 |
| 5,345,936 A | 9/1994 | Pomeranz et al. | |
| 5,348,554 A | 9/1994 | Imran et al. | |
| 5,354,297 A | 10/1994 | Avitall | |
| 5,370,644 A | 12/1994 | Langberg | |
| 5,383,923 A | 1/1995 | Webster, Jr. | |
| 5,389,073 A | 2/1995 | Imran | |
| 5,391,147 A | 2/1995 | Imran et al. | |
| 5,395,328 A | 3/1995 | Ockuly et al. | |
| 5,396,887 A | 3/1995 | Imran | |
| 5,397,304 A | 3/1995 | Truckai | |
| 5,405,376 A | 4/1995 | Mulier et al. | |
| 5,406,946 A | 4/1995 | Imran | |
| 5,409,000 A | 4/1995 | Imran | |
| 5,411,025 A | 5/1995 | Webster, Jr. | |
| 5,415,166 A | 5/1995 | Imran | |
| 5,423,772 A | 6/1995 | Lurie et al. | |
| 5,423,811 A | 6/1995 | Imran et al. | |
| 5,423,882 A | 6/1995 | Jackman et al. | |
| 5,431,168 A | 7/1995 | Webster, Jr. | |
| 5,431,649 A | 7/1995 | Mulier et al. | 606/41 |
| 5,433,708 A | 7/1995 | Nichols et al. | 604/113 |
| 5,445,148 A | 8/1995 | Jaraczewski et al. | |
| 5,465,717 A | 11/1995 | Imran et al. | |
| 5,478,330 A | 12/1995 | Imran et al. | |
| 5,487,385 A | 1/1996 | Avitall | |
| 5,487,757 A | 1/1996 | Truckai et al. | |
| 5,522,873 A | 6/1996 | Jackman et al. | |
| 5,527,279 A | 6/1996 | Imran | |
| 5,533,967 A | 7/1996 | Imran | |
| 5,540,681 A | 7/1996 | Strul et al. | |
| 5,542,928 A | 8/1996 | Evans et al. | 604/113 |
| 5,545,161 A | 8/1996 | Imran | |
| 5,545,200 A | 8/1996 | West et al. | |
| 5,549,581 A | 8/1996 | Lurie et al. | |
| 5,558,073 A | 9/1996 | Pomeranz et al. | |
| 5,562,619 A | 10/1996 | Mirarchi et al. | |
| 5,571,088 A | 11/1996 | Lennox et al. | |
| 5,573,533 A | 11/1996 | Strul | |
| 5,575,772 A | 11/1996 | Lennox | |
| 5,578,007 A | 11/1996 | Imran | |
| 5,582,609 A | 12/1996 | Swanson et al. | |
| 5,584,830 A | 12/1996 | Ladd et al. | |
| 5,584,872 A | 12/1996 | LaFontaine et al. | 607/116 |
| 5,588,964 A | 12/1996 | Imran et al. | |
| 5,609,151 A | 3/1997 | Mulier et al. | 128/642 |
| 5,611,777 A | 3/1997 | Bowden et al. | |
| 5,626,136 A | 5/1997 | Webster, Jr. | |
| 5,628,313 A | 5/1997 | Webster, Jr. | |
| 5,643,197 A * | 7/1997 | Brucker et al. | 604/20 |
| 5,643,231 A | 7/1997 | Lurie et al. | |
| 5,656,029 A | 8/1997 | Imran et al. | |
| 5,656,030 A | 8/1997 | Hunjan et al. | |
| 5,658,278 A | 8/1997 | Imran et al. | 606/41 |
| 5,676,662 A | 10/1997 | Fleischhacker et al. | |
| 5,676,693 A | 10/1997 | LaFontaine | 607/116 |
| 5,680,860 A | 10/1997 | Imran | |
| 5,697,927 A | 12/1997 | Imran et al. | 606/41 |
| 5,715,817 A | 2/1998 | Stevens-Wright et al. | |
| 5,722,401 A | 3/1998 | Pietroski et al. | |
| 5,722,963 A | 3/1998 | Lurie et al. | |
| 5,725,524 A | 3/1998 | Mulier et al. | 606/41 |
| 5,730,128 A | 3/1998 | Pomeranz et al. | |
| 5,755,760 A | 5/1998 | Maguire et al. | |
| 5,779,669 A | 7/1998 | Haissaguerre et al. | |
| 5,779,699 A | 7/1998 | Lipson | |
| 5,782,239 A | 7/1998 | Webster, Jr. | |
| 5,782,828 A | 7/1998 | Chen et al. | |
| 5,782,899 A | 7/1998 | Imran | |
| 5,785,706 A | 7/1998 | Bednarek | 606/41 |
| RE35,880 E | 8/1998 | Waldman et al. | |
| 5,792,140 A | 8/1998 | Tu et al. | |
| 5,800,482 A | 9/1998 | Pomeranz et al. | |
| 5,807,249 A | 9/1998 | Qin et al. | |
| 5,807,395 A | 9/1998 | Mulier et al. | |
| 5,814,029 A | 9/1998 | Hassett | |
| 5,820,568 A | 10/1998 | Willis | |
| 5,823,955 A | 10/1998 | Kuck et al. | |
| 5,826,576 A | 10/1998 | West | |
| 5,827,272 A | 10/1998 | Breining et al. | |
| 5,836,875 A | 11/1998 | Webster, Jr. | |
| 5,836,947 A | 11/1998 | Fleischman et al. | |
| 5,842,984 A | 12/1998 | Avitall | |
| 5,843,020 A | 12/1998 | Tu et al. | |
| 5,860,974 A | 1/1999 | Abele | |
| 5,865,800 A | 2/1999 | Mirarchi et al. | |
| 5,868,733 A | 2/1999 | Ockuly et al. | |
| 5,868,741 A | 2/1999 | Chia et al. | |
| 5,876,340 A | 3/1999 | Tu et al. | |
| 5,876,398 A | 3/1999 | Mulier et al. | 600/41 |
| 5,876,399 A | 3/1999 | Chia et al. | |
| 5,879,296 A | 3/1999 | Ockuly et al. | |
| 5,882,346 A | 3/1999 | Pomeranz et al. | |
| 5,885,278 A | 3/1999 | Fleischman et al. | |
| 5,891,027 A | 4/1999 | Tu et al. | |
| 5,891,137 A | 4/1999 | Chia et al. | |
| 5,893,885 A | 4/1999 | Webster, Jr. | |
| 5,895,355 A | 4/1999 | Schaer | |
| 5,895,417 A | 4/1999 | Pomeranz et al. | 607/101 |
| 5,897,529 A | 4/1999 | Ponzi | |
| 5,897,554 A | 4/1999 | Chia et al. | |
| 5,906,605 A | 5/1999 | Coxum | |
| 5,908,446 A | 6/1999 | Imran | |
| 5,910,129 A | 6/1999 | Koblish et al. | |
| 5,913,854 A * | 6/1999 | Maguire et al. | 606/41 |
| 5,913,856 A * | 6/1999 | Chia et al. | 606/41 |
| 5,916,158 A | 6/1999 | Webster, Jr. | |
| 5,916,213 A | 6/1999 | Haissaguerre et al. | |
| 5,916,214 A | 6/1999 | Cosio et al. | |
| 5,919,188 A | 7/1999 | Shearon et al. | 606/41 |
| 5,921,924 A | 7/1999 | Avitall | |
| 5,931,811 A | 8/1999 | Haissaguerre et al. | |
| 5,935,102 A | 8/1999 | Bowden et al. | |
| 5,935,124 A | 8/1999 | Klumb et al. | |
| 5,938,603 A | 8/1999 | Ponzi | |
| 5,938,659 A | 8/1999 | Tu et al. | |
| 5,938,660 A | 8/1999 | Swartz et al. | |
| 5,938,694 A | 8/1999 | Jaraczewski et al. | |
| 5,944,690 A | 8/1999 | Falwell et al. | |
| 5,951,471 A | 9/1999 | de la Rama et al. | |
| 5,964,796 A | 10/1999 | Imran | |
| 5,971,968 A | 10/1999 | Tu et al. | 604/264 |
| 5,971,983 A | 10/1999 | Lesh | |
| 5,987,344 A | 11/1999 | West | |
| 5,993,462 A | 11/1999 | Pomeranz et al. | |
| 5,997,532 A | 12/1999 | McLaughlin et al. | 606/41 |
| 6,001,085 A | 12/1999 | Lurie et al. | |
| 6,002,955 A | 12/1999 | Willems et al. | |
| 6,004,269 A | 12/1999 | Crowley et al. | |
| 6,010,500 A * | 1/2000 | Sherman et al. | 606/41 |

| Patent No. | Date | Inventor | Class |
|---|---|---|---|
| 6,012,457 A | 1/2000 | Lesh | |
| 6,014,579 A | 1/2000 | Pomeranz et al. | |
| 6,015,407 A | 1/2000 | Rieb et al. | 606/41 |
| 6,016,437 A | 1/2000 | Tu et al. | |
| 6,016,809 A | 1/2000 | Mulier et al. | 128/898 |
| 6,023,638 A | 2/2000 | Swanson | |
| 6,024,740 A | 2/2000 | Lesh et al. | |
| 6,027,473 A | 2/2000 | Ponzi | |
| 6,029,091 A | 2/2000 | de la Rama et al. | |
| 6,032,061 A | 2/2000 | Koblish | |
| 6,032,077 A | 2/2000 | Pomeranz | 607/101 |
| 6,033,403 A | 3/2000 | Tu et al. | |
| 6,048,329 A | 4/2000 | Thompson et al. | |
| 6,059,739 A | 5/2000 | Baumann | |
| 6,063,022 A | 5/2000 | Ben-Haim | |
| 6,063,080 A | 5/2000 | Nelson et al. | 606/41 |
| 6,064,902 A | 5/2000 | Haissaguerre et al. | |
| 6,064,905 A | 5/2000 | Webster, Jr. et al. | |
| 6,066,125 A | 5/2000 | Webster, Jr. | |
| 6,068,629 A | 5/2000 | Haissaguerre et al. | |
| 6,068,653 A | 5/2000 | LaFontaine | 607/116 |
| 6,071,274 A | 6/2000 | Thompson et al. | |
| 6,071,279 A | 6/2000 | Whayne et al. | |
| 6,071,282 A | 6/2000 | Fleischman | |
| 6,076,012 A | 6/2000 | Swanson et al. | |
| 6,078,830 A | 6/2000 | Levin et al. | |
| 6,080,151 A | 6/2000 | Swartz et al. | 606/45 |
| 6,083,222 A | 7/2000 | Klein et al. | |
| 6,090,104 A | 7/2000 | Webster, Jr. | |
| 6,117,101 A | 9/2000 | Diederich et al. | |
| 6,119,041 A | 9/2000 | Pomeranz et al. | 607/101 |
| 6,120,476 A | 9/2000 | Fung et al. | 604/95 |
| 6,120,500 A * | 9/2000 | Bednarek et al. | 606/41 |
| 6,123,699 A | 9/2000 | Webster, Jr. | |
| 6,132,426 A | 10/2000 | Kroll | 606/41 |
| 6,138,043 A | 10/2000 | Avitall | |
| 6,146,338 A | 11/2000 | Gardeski et al. | |
| 6,156,034 A | 12/2000 | Cosio et al. | |
| 6,164,283 A | 12/2000 | Lesh | |
| 6,168,594 B1 | 1/2001 | LaFontaine et al. | 606/41 |
| 6,169,916 B1 | 1/2001 | West | |
| 6,171,275 B1 | 1/2001 | Webster, Jr. | 604/20 |
| 6,171,277 B1 | 1/2001 | Ponzi | |
| 6,183,435 B1 | 2/2001 | Bumbalough et al. | |
| 6,183,463 B1 | 2/2001 | Webster, Jr. | |
| 6,198,974 B1 | 3/2001 | Webster, Jr. | |
| 6,200,315 B1 | 3/2001 | Gaiser et al. | |
| 6,203,507 B1 | 3/2001 | Wadsworth et al. | |
| 6,203,525 B1 | 3/2001 | Whayne et al. | |
| 6,210,362 B1 | 4/2001 | Ponzi | |
| 6,210,406 B1 | 4/2001 | Webster | |
| 6,210,407 B1 | 4/2001 | Webster | |
| 6,214,002 B1 | 4/2001 | Fleischman et al. | |
| 6,217,528 B1 | 4/2001 | Koblish et al. | |
| 6,217,573 B1 | 4/2001 | Webster | |
| 6,217,574 B1 | 4/2001 | Webster | |
| 6,217,576 B1 | 4/2001 | Tu et al. | 606/41 |
| 6,219,582 B1 | 4/2001 | Hofstad et al. | 607/122 |
| 6,221,070 B1 | 4/2001 | Tu et al. | |
| 6,224,587 B1 | 5/2001 | Gibson | |
| 6,233,477 B1 | 5/2001 | Chia et al. | |
| 6,235,022 B1 | 5/2001 | Hallock et al. | 606/41 |
| 6,235,025 B1 | 5/2001 | Swartz et al. | |
| 6,235,044 B1 * | 5/2001 | Root et al. | 606/200 |
| 6,238,393 B1 | 5/2001 | Mulier et al. | 606/41 |
| 6,241,722 B1 | 6/2001 | Dobak et al. | 606/23 |
| 6,241,726 B1 | 6/2001 | Chia et al. | |
| 6,241,727 B1 | 6/2001 | Tu et al. | |
| 6,241,754 B1 | 6/2001 | Swanson et al. | |
| 6,245,064 B1 | 6/2001 | Lesh et al. | |
| 6,251,109 B1 * | 6/2001 | Hassett et al. | 606/45 |
| 6,254,599 B1 | 7/2001 | Lesh et al. | |
| 6,264,654 B1 | 7/2001 | Swartz et al. | |
| 6,287,306 B1 | 9/2001 | Kroll et al. | |
| 6,290,697 B1 | 9/2001 | Tu et al. | |
| 6,305,378 B1 | 10/2001 | Lesh | |
| 6,308,091 B1 | 10/2001 | Avitall | |
| 6,314,962 B1 | 11/2001 | Vaska et al. | |
| 6,314,963 B1 | 11/2001 | Vaska et al. | |
| 6,325,797 B1 | 12/2001 | Stewart et al. | |
| 6,330,473 B1 | 12/2001 | Swanson et al. | |
| 6,371,955 B1 | 4/2002 | Fuimaono et al. | |
| 6,375,654 B1 | 4/2002 | McIntyre | |
| 6,383,151 B1 | 5/2002 | Diederich et al. | |
| 6,391,024 B1 | 5/2002 | Sun et al. | |
| 6,402,746 B1 | 6/2002 | Whayne et al. | |
| 6,409,722 B1 | 6/2002 | Hoey et al. | 606/34 |
| 6,416,511 B1 | 7/2002 | Lesh et al. | |
| 6,447,507 B1 | 9/2002 | Bednarek et al. | |
| 6,454,758 B1 | 9/2002 | Thompson et al. | |
| 6,454,766 B1 | 9/2002 | Swanson et al. | 606/41 |
| 6,466,811 B1 | 10/2002 | Hassett | |
| 6,500,174 B1 * | 12/2002 | Maguire et al. | 606/41 |
| 6,503,247 B2 | 1/2003 | Swartz et al. | |
| 6,522,930 B1 * | 2/2003 | Schaer et al. | 607/101 |
| 6,540,744 B2 | 4/2003 | Hassett et al. | |
| 6,605,087 B2 | 8/2003 | Swartz et al. | 606/41 |
| 6,692,492 B2 | 2/2004 | Simpson et al. | |
| 6,702,811 B2 * | 3/2004 | Stewart et al. | 606/41 |
| 6,837,886 B2 | 1/2005 | Collins et al. | |
| 6,858,026 B2 | 2/2005 | Sliwa et al. | 606/28 |
| 6,960,207 B2 * | 11/2005 | Vanney et al. | 606/41 |
| 7,029,471 B2 * | 4/2006 | Thompson et al. | 606/41 |
| 2002/0026187 A1 | 2/2002 | Swanson | |
| 2003/0125726 A1 * | 7/2003 | Maguire et al. | 606/41 |
| 2004/0143255 A1 * | 7/2004 | Vanney et al. | 606/41 |
| 2004/0143256 A1 * | 7/2004 | Bednarek | 606/41 |
| 2004/0181189 A1 | 9/2004 | Roychowdhury et al. | |
| 2005/0055019 A1 | 3/2005 | Skarda | |

* cited by examiner

ABLATION CATHETER WITH FLUID DISTRIBUTION STRUCTURES

BACKGROUND OF THE INVENTION a. Field of the Invention

The instant invention is directed toward a catheter with an electrode section including a fluid distribution structure for ablation of tissue. In certain embodiments, the electrode section may include structures, for example, mesh grating and porous materials, that evenly distribute conductive fluid for improved consistency in fluid flow from the catheter across the electrode section to effect a uniform virtual electrode.

b. Background Art

Catheters have been in use for medical procedures for many years. Catheters can be used for medical procedures to examine, diagnose, and treat while positioned at a specific location within the body that is otherwise inaccessible without more invasive procedures. During these procedures a catheter is inserted into a vessel near the surface of the body and is guided to a specific location within the body for examination, diagnosis, and treatment. For example, one procedure utilizes a catheter to convey an electrical stimulus to a selected location within the human body. Another procedure utilizes a catheter with sensing electrodes to monitor various forms of electrical activity in the human body.

Catheters are also used increasingly for medical procedures involving the human heart. Typically, the catheter is inserted in an artery or vein in the leg, neck, or arm of the patient and threaded, sometimes with the aid of a guide wire or introducer, through the vessels until a distal tip of the catheter reaches the desired location for the medical procedure in the heart.

A typical human heart includes a right ventricle, a right atrium, a left ventricle, and a left atrium. The right atrium is in fluid communication with the superior vena cava and the inferior vena cava. The atrioventricular septum separates the right atrium from the right ventricle. The tricuspid valve contained within the atrioventricular septum provides communication between the right atrium and the right ventricle.

In the normal heart, contraction and relaxation of the heart muscle (myocardium) takes place in an organized fashion as electro-chemical signals pass sequentially through the myocardium from the sinoatrial (SA) node, which comprises a bundle of unique cells disposed in the wall of the right atrium, to the atrioventricular (AV) node and then along a well-defined route, which includes the His-Purkinje system, into the left and right ventricles. The AV node lies near the ostium of the coronary sinus in the interatrial septum in the right atrium. Each cell membrane of the SA node has a characteristic tendency to leak sodium ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole, wherein the atria contract to empty and fill blood into the ventricles. The atrial depolarization from the SA node is detected by the AV node which, in turn, communicates the depolarization impulse into the ventricles via the bundle of His and Purkinje fibers following a brief conduction delay. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart, which are referred to generally as arrhythmia. For example, a common arrhythmia is Wolff-Parkinson-White syndrome (W-P-W). The cause of W-P-W is generally believed to be the existence of an anomalous conduction pathway or pathways that connect the atrial muscle tissue directly to the ventricular muscle tissue, thus bypassing the normal His-Purkinje system. These pathways are usually located in the fibrous tissue that connects the atrium and the ventricle.

Other abnormal arrhythmias sometimes occur in the atria, which are referred to as atrial arrhythmia. Three of the most common atrial arrhythmia are ectopic atrial tachycardia, atrial fibrillation, and atrial flutter. Atrial fibrillation can result in significant patient discomfort and even death because of a number of associated problems, including the following: an irregular heart rate, which causes patient discomfort and anxiety; loss of synchronous atrioventricular contractions, which compromises cardiac hemodynamics, resulting in varying levels of congestive heart failure; and stasis of blood flow, which increases the likelihood of thromboembolism.

Efforts to alleviate these problems in the past have included significant usage of pharmacological treatments. While pharmacological treatments are sometimes effective, in some circumstances drug therapy has had only limited effectiveness and is frequently plagued with side effects, such as dizziness, nausea, vision problems, and other difficulties.

An increasingly common medical procedure for the treatment of certain types of cardiac arrhythmia is catheter ablation. During conventional catheter ablation procedures, an energy source is placed in contact with cardiac tissue to heat the tissue and create a permanent scar or lesion that is electrically inactive or noncontractile. During one procedure, the lesions are designed to interrupt existing conduction pathways commonly associated with arrhythmias within the heart. The particular area for ablation depends on the type of underlying arrhythmia. One common ablation procedure treats atrioventricular nodal reentrant tachycardia (AVNRT). Ablation of fast or slow AV nodal pathways is disclosed in Singer, I., et al., "Catheter Ablation for Arrhythmias," Clinical Manual of Electrophysiology, pgs. 421-431 (1993).

Another medical procedure using ablation catheters with sheaths to ablate accessory pathways associated with W-P-W utilizing both a transseptal and retrograde approach is discussed in Saul, J. P., et al., "Catheter Ablation of Accessory Atrioventricular Pathways in Young Patients: Use of long vascular sheaths, the transseptal approach and a retrograde left posterior parallel approach," Journal of the American College of Cardiology, Vol. 21, no. 3, pgs. 571-583 (1 Mar. 1993). Other catheter ablation procedures are disclosed in Swartz, J. F., "Radiofrequency Endocardial Catheter Ablation of Accessory Atrioventricular Pathway Atrial Insertion Sites," Circulation, Vol. 87, no. 2, pgs. 487-499 (February 1993).

Ablation of a specific location within or near the heart requires the precise placement of the ablation catheter. Precise positioning of the ablation catheter is especially difficult because of the physiology of the heart, particularly because the heart continues to beat throughout the ablation procedures. Commonly, the choice of placement of the catheter is determined by a combination of electrophysiological guidance and fluoroscopy (placement of the catheter in relation to known features of the heart, which are marked by radiopaque diagnostic catheters that are placed in or at known anatomical structures, such as the coronary sinus, high right atrium, and the right ventricle).

The energy necessary to ablate cardiac tissue and create a permanent lesion can be provided from a number of different sources. Originally, direct current was utilized although laser, microwave, ultrasound, and other forms of energy have also been utilized to perform ablation procedures. Because of problems associated with the use of direct current, however, radio frequency (RF) has become the preferred source of energy for ablation procedures. The use of RF energy with an ablation catheter contained within a transseptal sheath for the treatment of W-P-W in the left atrium is disclosed in Swartz, J. F. et al., "Radiofrequency Endocardial Catheter Ablation of Accessory Atrioventricular Pathway Atrial Insertion Sites," Circulation, Vol. 87, pgs. 487-499 (1993). See also Tracey, C. N., "Radio Frequency Catheter Ablation of Ectopic Atrial Tachycardia Using Paced Activation Sequence Mapping," J. Am. Coll. Cardiol. Vol. 21, pgs. 910-917 (1993).

In addition to RF ablation catheters, thermal ablation catheters have been used. During thermal ablation procedures, a heating element, secured to the distal end of a catheter, heats thermally conductive fluid, which fluid then contacts the human tissue to raise its temperature for a sufficient period of time to ablate the tissue.

Conventional ablation procedures utilize a single distal electrode secured to the tip of an ablation catheter. Increasingly, however, cardiac ablation procedures utilize multiple electrodes affixed to the catheter body. These ablation catheters often contain a distal tip electrode and a plurality of ring electrodes.

To form linear lesions within the heart using a conventional ablation tip electrode requires the utilization of procedures such as a "drag burn." The term "linear lesion" as used herein means an elongate, continuous lesion, whether straight or curved, that blocks electrical conduction. During a "drag burn" procedure, while ablating energy is supplied to the tip electrode, the tip electrode is drawn across the tissue to be ablated, producing a line of ablation. Alternatively, a series of points of ablation are formed in a line created by moving the tip electrode incremental distances across the cardiac tissue. The effectiveness of these procedures depends on a number of variables including the position and contact pressure of the tip electrode of the ablation catheter against the cardiac tissue, the time that the tip electrode of the ablation catheter is placed against the tissue, the amount of coagulum that is generated as a result of heat generated during the ablation procedure, and other variables associated with a beating heart, especially an erratically beating heart. Unless an uninterrupted track of cardiac tissue is ablated, unablated tissue or incompletely ablated tissue may remain electrically active, permitting the continuation of the stray circuit that causes the arrhythmia.

It has been discovered that more efficient ablation may be achieved if a linear lesion of cardiac tissue is formed during a single ablation procedure. The ablation catheters commonly used to perform these ablation procedures produce electrically inactive or noncontractile tissue at a selected location by physical contact of the cardiac tissue with an electrode of the ablation catheter. Conventional tip electrodes with adjacent ring electrodes cannot perform this type of procedure, however, because of the high amount of energy that is necessary to ablate sufficient tissue to produce a complete linear lesion. Also, conventional ring electrode ablation may leave holes or gaps in a lesion, which can provide a pathway along which unwanted electrochemical signals can travel.

During conventional ablation procedures, the ablating energy is delivered directly to the cardiac tissue by an electrode on the catheter placed against the surface of the tissue to raise the temperature of the tissue to be ablated. This rise in tissue temperature also causes a rise in the temperature of blood surrounding the electrode. This often results in the formation of coagulum on the electrode, which reduces the efficiency of the ablation electrode. With direct contact between the electrode and the blood, some of the energy targeted for the tissue ablation is dissipated into the blood. To achieve efficient and effective ablation, coagulation of blood that is common with conventional ablation catheters should be avoided. This coagulation problem can be especially significant when linear ablation lesions or tracks are produced because such linear ablation procedures conventionally take more time than ablation procedures ablating only a single location.

To address the coagulation concern, more recent designs of ablation electrodes transfer energy to the target tissue with a conductive fluid medium that passes over a standard metal electrode rather than contacting the standard electrode to the tissue. The fluid flow thus reduces the likelihood that coagulum will form on any of the surfaces of the electrode. These so-called "virtual electrodes" also help reduce tissue charring because the fluid, while energized, also acts as a cooling heat transfer medium. However, with present virtual electrode designs, the fluid flow is not often uniform, resulting in hot spots due greater energy transfer in areas with greater flow. Further, with present virtual electrode designs, the volume of fluid flow required to create a lesion is very high and thus introduces a significant amount of excess fluid into the patient's vasculature, which can significantly dilute the patient's blood volume and compromise pulmonary circulation capacity.

In some instances, stray electrical signals find a pathway down the pulmonary veins and into the left atrium of the heart. In these instances, it may be advantageous to produce a circumferential lesion at or near the ostium of one or more of the pulmonary veins. Desirably, such a circumferential lesion would electrically isolate a pulmonary vein from the left atrium, completely blocking stray signals from traveling down the pulmonary vein and into the left atrium. It is desirable to have a catheter with a distal portion for forming such circumferential lesions in tissue while avoiding problems with existing designs.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

The present invention is directed to an ablation catheter with improved fluid distribution structures. An ablation section at a distal end of the catheter is designed to provide a more uniform fluid flow emanating from the catheter. By creating a uniform fluid flow, a more uniform tissue lesion results and the possibility of charring the tissue is reduced. A combination of mesh material layers, porous materials, and dispersion channels or openings are used to achieve the uniform flow. The amount of fluid used as a virtual electrode to ablate the tissue is greatly reduced with the present invention. Further, the catheter may be used to create a single, uniform linear lesion by successive application of energy to adjacent portions of the ablation section, thus reducing the power required to create the desired lesion.

In one embodiment of the invention, a catheter is composed of a proximal section and an ablation section at a distal end of the catheter. A catheter wall defines at least one fluid lumen extending from the proximal section to the ablation section. An electrode lead is positioned within the at least one fluid lumen extending within the ablation section. At least one dispersion opening is positioned within the catheter wall in the ablation section and is oriented longitudinally along a length of the ablation section. The at least one dispersion opening is in fluid communication with the at least one fluid lumen. A length of mesh material is generally coextensive with and positioned adjacent to the at least one dispersion opening on the opposing side of the at least one dispersion opening from the at least one fluid lumen.

In another embodiment of the invention, a catheter with a distal ablation electrode tip is again composed of a proximal section and an ablation section at a distal end of the catheter. A catheter wall defines at least one fluid lumen extending from the proximal section to the ablation section. At least one dispersion opening is formed within the catheter wall in the ablation section and is oriented longitudinally along a length of the ablation section. The at least one dispersion opening is in fluid communication with the at least one fluid lumen. An irrigation cavity is positioned within the ablation section of the catheter. An elongate opening is formed in an outside surface of the catheter wall in fluid communication with the irrigation cavity. The at least one dispersion opening provides fluid communication between the at least one fluid lumen and the irrigation cavity. A tube-shaped, conductive mesh material is generally coextensive with and positioned within the irrigation cavity. A porous material is positioned within and fills a lumen of the tube-shaped, conductive mesh material. An electrode lead is coupled with the tube-shaped, conductive mesh material.

In an alternate embodiment of the invention, a catheter with a distal ablation electrode tip is again composed of a proximal section and an ablation section at a distal end of the catheter. A catheter wall defines at least one fluid lumen extending from the proximal section to the ablation section. An irrigation cavity is formed by the distal end of the fluid lumen within the ablation section of the catheter. A tube-shaped, conductive mesh material is generally coextensive with and positioned within the irrigation cavity. The tube-shaped, conductive mesh material has a first outer diameter and a first inner diameter. The first outer diameter is sized to fit snugly within an inner diameter of the irrigation cavity. A tube-shaped porous material has a second outer diameter and a second inner diameter. The second outer diameter is sized to fit snugly within the first inner diameter of the first tube. An elongate opening is formed in an outside surface of the catheter wall in fluid communication with the irrigation cavity. An electrode lead is coupled with the tube-shaped, conductive mesh material.

In a further embodiment of the invention, a catheter with a distal ablation electrode tip is again composed of a proximal section and an ablation section at a distal end of the catheter. A catheter wall defines a first fluid lumen extending from the proximal section to the ablation section. A second fluid lumen extends from the proximal section to the ablation section. An irrigation cavity is positioned within the ablation section of the catheter. An insulating plug is positioned within the irrigation cavity and separates the irrigation cavity into a proximal portion and a distal portion. A first dispersion opening is formed within the catheter wall in the ablation section and is oriented longitudinally along a length of the ablation section. The first dispersion opening is in fluid communication with both the first fluid lumen and the proximal portion of the irrigation cavity. A second dispersion opening is formed within the catheter wall in the ablation section oriented longitudinally along a length of the ablation section. The second dispersion opening is in fluid communication with both the second fluid lumen and the distal portion of the irrigation cavity. An elongate opening is formed in an outside surface of the catheter wall in fluid communication with the irrigation cavity. The elongate opening is subdivided into a proximal opening and a distal opening, which are separated by a bridge member. The proximal opening is generally coextensive with the proximal portion of the irrigation cavity. The distal opening is generally coextensive with the distal portion of the irrigation cavity. The bridge member connects a top edge of the elongate opening to a bottom edge of the elongate opening. A first tube-shaped, conductive mesh section is generally coextensive with and positioned within the proximal portion of the irrigation cavity. A second tube-shaped, conductive mesh section is generally coextensive with and positioned within the distal portion of the irrigation cavity. The first tube-shaped, conductive mesh section is electrically insulated from the second tube-shaped, conductive mesh section by the insulating plug. A first porous material section is positioned within and fills the first tube-shaped, conductive mesh section. A second porous material section is positioned within and fills the second tube-shaped, conductive mesh section. The first porous material section is fluidly isolated from the second porous material section by the insulating plug. An electrode lead is coupled with the tube-shaped, conductive mesh material.

Another aspect of the invention is a method for creating a uniform flow of a fluid emanating from an ablation section at a distal end of a catheter. The method involves first flowing a conductive fluid through a lumen in the catheter. This creates a first pressure drop across the conductive fluid in the lumen between a proximal end of the catheter and the ablation section. Next the conductive fluid flows from the lumen through a porous material positioned in the ablation section. This creates a second pressure drop between a first surface of the porous material and a second surface of the porous material. The second pressure drop through the porous material is higher than the first pressure drop. Finally; the conductive fluid flows through a mesh electrode adjacent the porous material.

Other features, details, utilities, and advantages of the present invention will be apparent from the following more particular written description of various embodiments of the invention as further illustrated in the accompanying drawings and defined in the appended claims.

DETAILED DESCRIPTION OF THE INVENTION

The present invention concerns an improved design for ablation catheters used, for example, in cardiac ablation procedures to produce linear lesions in cardiac tissue. The electrode structure on the distal end of the catheter of the present invention is generally termed a "virtual electrode" as ablation energy is primarily imparted to the target tissue via energy transfer through a conductive fluid medium escaping the distal end of the catheter rather than by actual contact of a traditional electrode with the tissue. The present invention is primarily directed to improving the uniformity of fluid flow from the electrode structure in order to achieve greater uniformity in lesions created in the target tissue.

Figure 1:
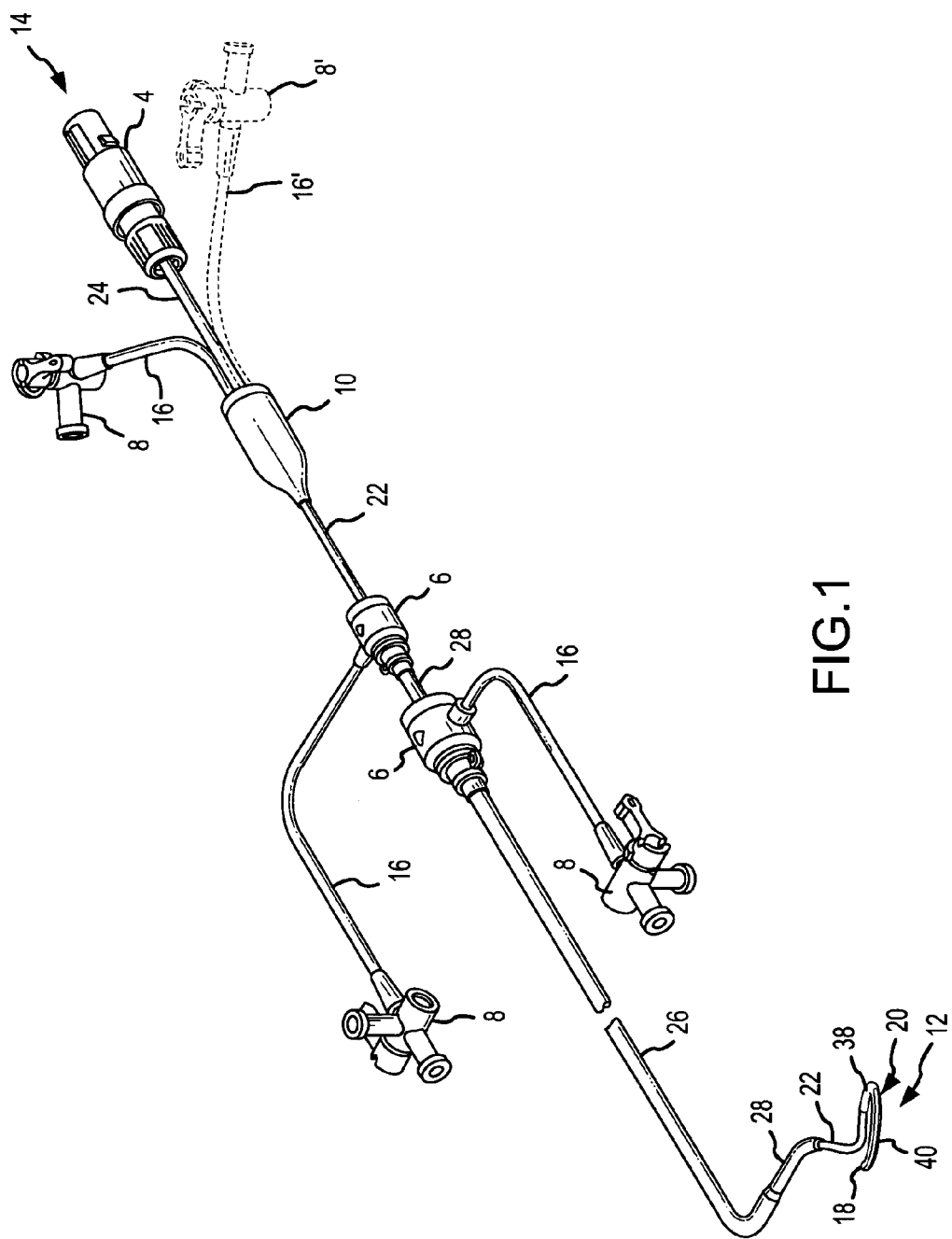
FIG. 1 is an isometric view of a catheter/introducer assembly including an ablation tip according to a generic embodiment of the present invention.

FIG. 1 is an isometric view of a catheter/introducer assembly 2 for use in conjunction with the present invention. A catheter 22 with a handle interface 4 at a proximal end 14 and an ablation electrode section 20, according to a generic embodiment of the present invention, at a distal end 12 is used in combination with an inner guiding introducer 28 and an outer guiding introducer 26 to facilitate formation of lesions on tissue, for example, cardiovascular tissue. The inner guiding introducer 28 is longer than and is inserted within the lumen of the outer guiding introducer 26. Alternatively, a single guiding introducer or a precurved transeptal sheath may be used instead of both the inner guiding introducer 28 and the outer guiding introducer 26. In general, introducers or precurved sheaths are shaped to facilitate placement of the ablation electrode section 20 at the tissue surface to be ablated. As depicted in FIG. 1, for example, the outer guiding introducer 26 may be formed with a curve at the distal end 12. Similarly, the inner guiding introducer 28 may be formed with a curve at the distal end 12. Together, the curves in the guiding introducers 26, 28 help orient the catheter 22 as it emerges from the inner guiding introducer 26 in a cardiac cavity. Thus, the inner guiding introducer 28 and the outer guiding introducer 26 are used navigate a patient's vasculature to the heart and through its complex physiology to reach specific tissue to be ablated. The guiding introducers 26, 28 need not be curved or curved in the manner depicted depending upon the desired application.

As shown in FIG. 1, each of the guiding introducers 26, 28 is connected with a hemostatic valve 6 at its proximal end to prevent blood or other fluid that fills the guiding introducers 26, 28 from leaking before the insertion of the catheter 22. The hemostatic valves 6 form tight seals around the shafts of the guiding introducers 26, 28 or the catheter 22 when inserted therein. Each hemostatic valve 6 may be have a port connected with a length of tubing 16 to a fluid introduction valve 8. The fluid introduction valves 8 may be connected with a fluid source, for example, saline or a drug, to easily introduce the fluid into the introducers, for example, to flush the introducer or to inject a drug in to the patient. Each of the fluid introduction valves 8 may control the flow of fluid into the hemostatic valves 16 and thereby the guiding introducers 26, 28.

The proximal end 14 of the catheter 22 may include a catheter boot 10 that seals around several components to allow the introduction of fluids and control mechanisms into the catheter 22. For example, at least one fluid introduction valve 8 with an attached length of tubing 16 may be coupled with the catheter boot 10. An optional fluid introduction valve 8' and correlative tube 16' (shown in phantom) may also be coupled with the catheter boot 10, for example, for the introduction of fluid into a catheter with multiple fluid lumens if separate control of the pressure and flow of fluid in the separate lumens is desired. A handle interface 4 for connection with a control handle, a generator, and/or sensing equipment (none shown) may be coupled with the catheter boot 10 via a control shaft 24. The control shaft 24 may enclose, for example, control wires for manipulating the catheter 22 or ablation electrode section 20, conductors for energizing an electrode in the ablation electrode section 20, and/or lead wires for connecting with sensors in the ablation electrode section 20. The catheter boot 10 provides a sealed interface to shield the connections between such wires and fluid sources and one or more lumen in the catheter 22 through which they extend.

The distal end of the catheter may be straight or take on a myriad of shapes depending upon the desired application. The distal end 12 of one embodiment of a catheter 122 according to the present invention is shown in greater detail in FIG. 2. In the embodiment shown in FIG. 2, the catheter 122 consists mainly of a "straight" section 30 extending from the catheter boot 10 at the proximal end 14 to a point adjacent to the distal end 12 of the catheter/introducer assembly 2 (see the exemplary catheter of FIG. 1). At the distal end 12 the catheter 122 is composed of a first curved section 32 and a second curved section 34 before transitioning into a third curved section 36 that forms the ablation electrode. The first curved section 32 is adjacent and distal to the straight section 30 and proximal and adjacent to the second curved section 34. The second curved section 34 is itself proximal and adjacent to the third curved section 36. The straight section 30, first curved section 32, second curved section 34, and third curved section may together form a single, unitary structure of the catheter 122, but may originally be separate pieces joined together to form the catheter 122.

Each of the different sections of the catheter may be constructed from a number of different polymers, for example, polypropylene, oriented polypropylene, polyethylene, polyethylene terephthalate, crystallized polyethylene terephthalate, polyester, polyvinyl chloride, and Pellethane®. Alternatively, the different sections of the catheter may be composed, for example, of different formulations of Pebax® resins (AUTOFINA Chemicals, Inc. Philadelphia, Pa.), or other polyether-block co-polyamide polymers, which can be used to create desired materials stiffness within the different sections of the catheter. By using different formulations of the Pebax® resins, different mechanical properties (e.g., flexibility or stiffness) can be chosen for each of the sections along a catheter.

The catheter may also be a braided catheter wherein the catheter wall includes a cylindrical braid of metal fibers, for example, stainless steel fibers. Such a metallic braid may be included in the catheter to add stability to the catheter and also to resist radial forces that might crush the catheter. Metallic braid also provides a framework to translate torsional forces imparted by the clinician on the proximal end of the catheter to the distal end to rotate the catheter for appropriate orientation of the ablation electrode.

Figure 2:
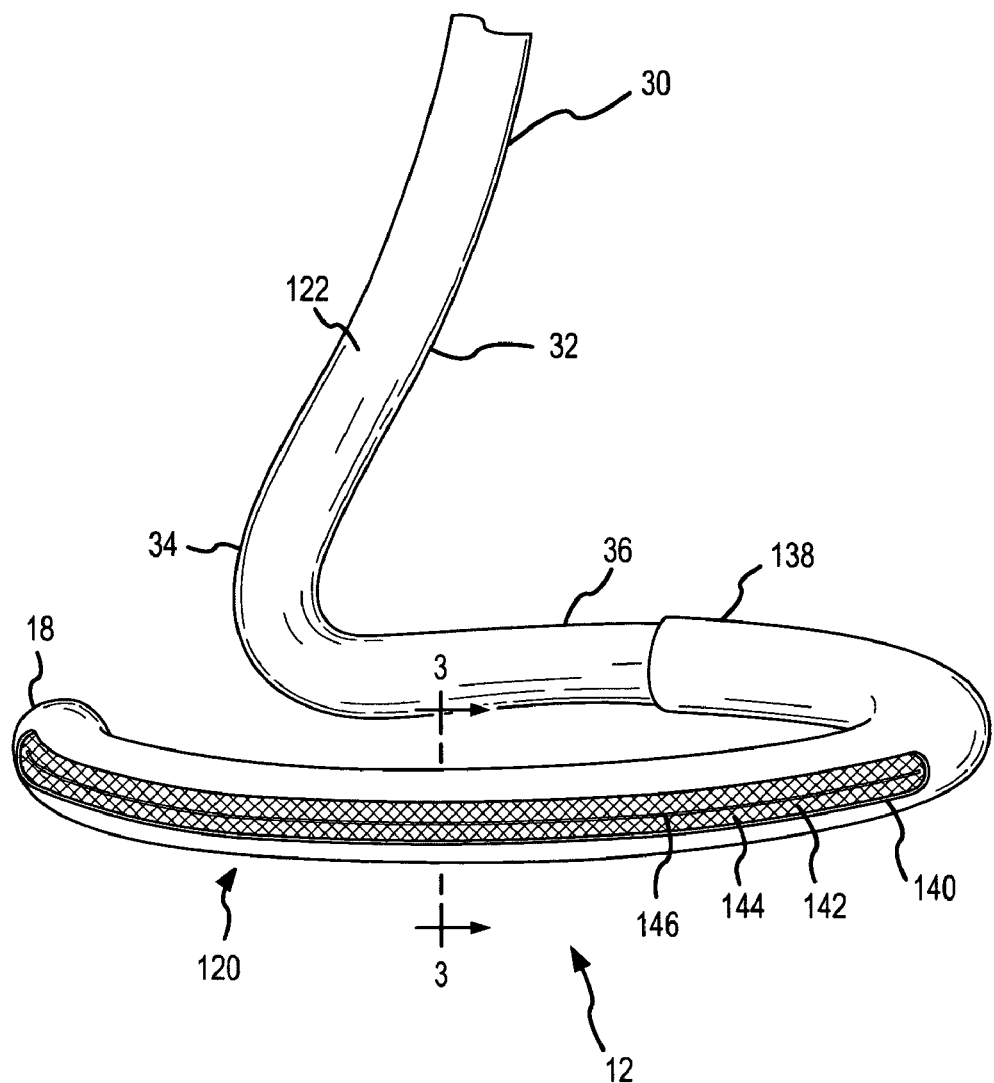
FIG. 2 is an isometric view of a distal portion of a catheter, including an ablation tip, according to one embodiment of the present invention.

The straight section 30 is generally the portion of the catheter 122 that remains within the vasculature of the patient while a sensing or ablation procedure is performed by a clinician. As shown in FIG. 2, the ablation electrode section 120 make assume a generally circular or C-shaped configuration when deployed from the inner guiding introducer 28. The first curved section 32 and second curved section 34 of the catheter 122 align the straight section 30 of the catheter 122 with respect to the third curved section 36. In particular, the distal end of the straight section 30 of the catheter 122 is oriented in a position where a longitudinal axis extending through the distal end of the straight section 30 passes orthogonally through the center of a circle defined by the C-shaped third curved section 36. In this manner the straight section 30 of the catheter 122 is spatially displaced from the ablation electrode section 120 so that the straight section 30 is unlikely to interfere with the interface between the ablation electrode on the third curved section 36 and the cardiac tissue as further described below.

In addition to a particular form for the distal end of the catheter 122, FIG. 2 also depicts a first embodiment of an ablation electrode section 120 according to the present invention. In this embodiment, the distal end 12 of the catheter 122 is covered by a retention layer, for example, a length of shrink tubing 138. An elongate aperture 140 is formed within a wall of the shrink tubing 138 and extends along the length of the shrink tubing 138 to a position adjacent the distal tip 18 of the catheter 122. Revealed within the elongate aperture 140 is a mesh material 142 that is positioned upon an outer surface of the catheter wall 144 and is held in place by the shrink tubing 138. A dispersion slot 146 is formed within the catheter wall 144 coincident with the position and length of the elongate aperture 140 in the shrink tubing 138. The mesh material 142 is slightly larger in area than the each of the elongate aperture 140 and the dispersion slot 146 such that the edges of the mesh material 142 are clamped between the catheter wall 144 and the shrink tubing 138. Each of these structures may be seen to better advantage in the cross-sections of FIGS. 3 and 4.

Figure 3:
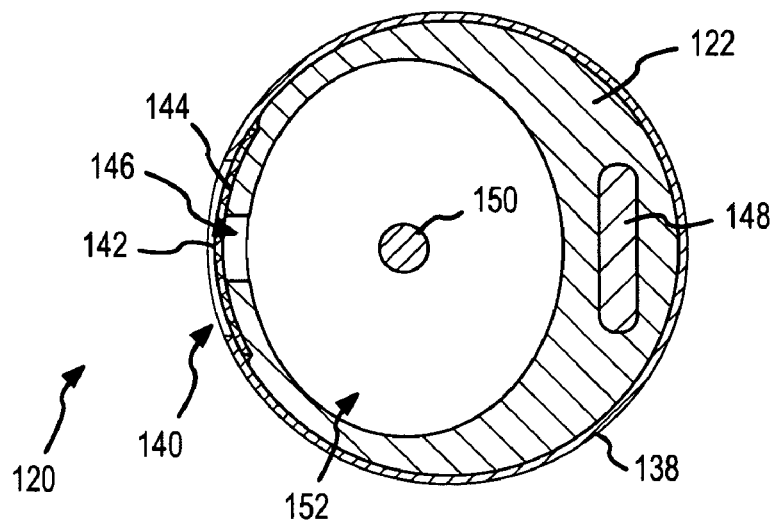
FIG. 3 is a cross-section of the catheter of FIG. 2 along line 3-3 as indicated in FIG. 2.

As shown to good advantage in FIG. 3, the catheter 122 defines a large fluid lumen 152 that is in fluid communication with the dispersion slot 146 and the catheter wall 144. An electrode lead 150 may be positioned within the fluid lumen 152 to impart ablation energy, generally RF energy, to conductive fluid, e.g., isotonic saline, in the lumen 152 adjacent the dispersion slot 146. The catheter 122 may further house a shape-retention or shape-memory wire 148 in order to impart a desired shape to the distal end 12 of the catheter 122 in the area of the ablation electrode section 120.

When the electrode 150 is energized the energy is transferred to the conductive fluid in the fluid lumen 152. The conductive fluid is forced by the fluid pressure within the fluid lumen 152 sequentially through the dispersion slot 146 in the catheter wall 144, then through the mesh material 142, and finally exits ablation electrode section 120 through the elongate aperture 140. The dispersion slot 146 and the mesh material 142 together act to evenly distribute the conductive fluid as it exists the ablation electrode section 120 portion of the catheter 122. In this manner, a uniform ablation lesion may be formed in tissue adjacent the elongate aperture 148 and the shrink tubing 138 where the energized conductive fluid exists the ablation electrode 120.

In the present embodiment, as well as in further embodiments described herein, the mesh material may have on the order of between 5 and 2,000 holes per linear inch. The mesh material is provided to improve the uniformity of distribution of the fluid along the length of the ablation electrode section, which enhances the uniformity of the corresponding tissue lesion. In one embodiment, the when using a catheter with a braided wall construction, the mesh material may even be the metallic braid in the catheter wall. As this suggests, the mesh material may additionally be a conductive material, for example, platinum, platinum/iridium, and gold. Alternatively, the mesh material may be a carbon fiber mesh. Braided metal wire, e.g., stainless steel wire, may also be used as the mesh material. Because the conductive fluid in the lumen is in contact with both the electrode lead and the conductive mesh material, the mesh material becomes a secondary electrode. The high electrical conductivity of the mesh material in such an embodiment, the voltage along the entire length of the mesh material is highly uniform, again contributing to greater uniformity in the tissue lesion. The uniform flow of the conductive fluid across the mesh material acts as a cooling medium as well, which, in conjunction with the constant voltage of the mesh material, helps to maintain a fairly uniform temperature along the length of the ablation electrode section, which further contributes to uniformity in the resulting tissue lesion. If may also be desirable to include a temperature sensor in the mesh material to monitor the temperature on the surface of the mesh material. Such temperature information can allow a clinician to adjust the power of the RF energy, the fluid flow, or both to provide greater control over the depth and uniformity of the resulting tissue lesion.

Figure 4:
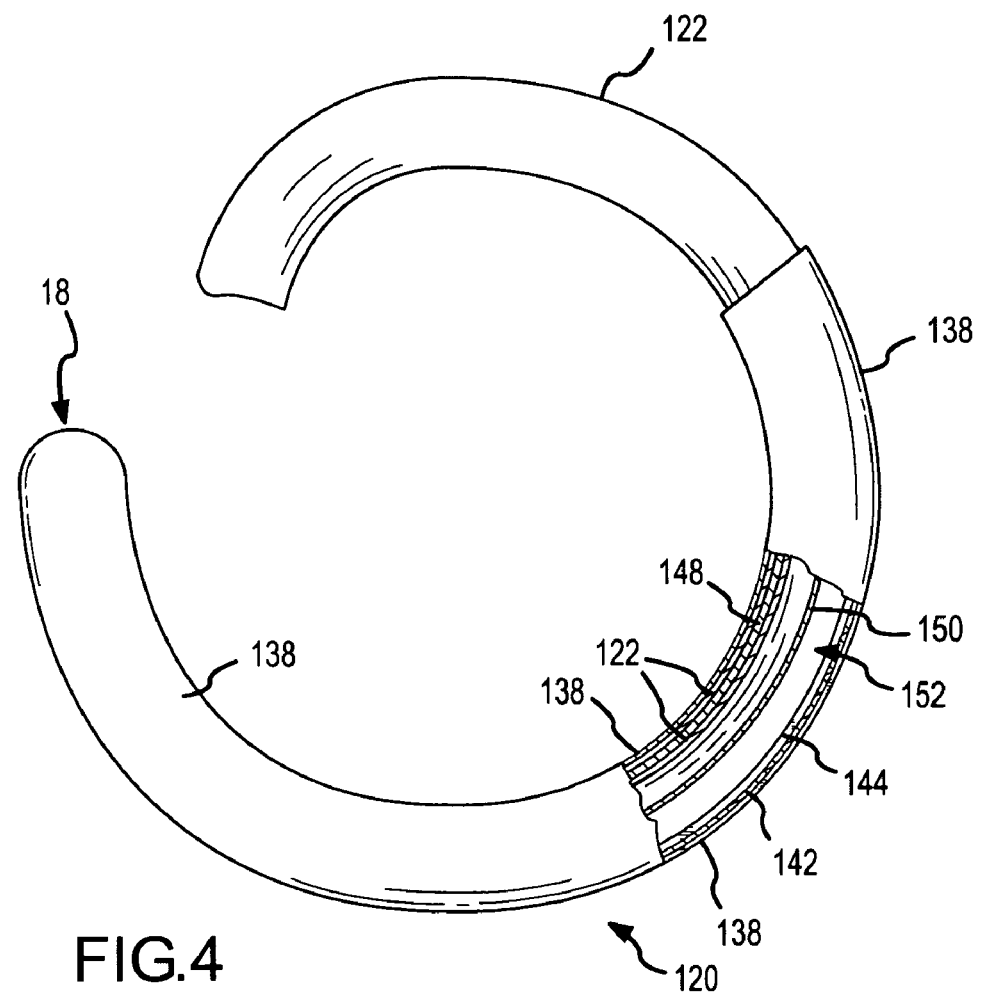
FIG. 4 is a bottom plan view with a partial cut-away of a distal portion of the catheter of FIG. 2.
Figure 19:
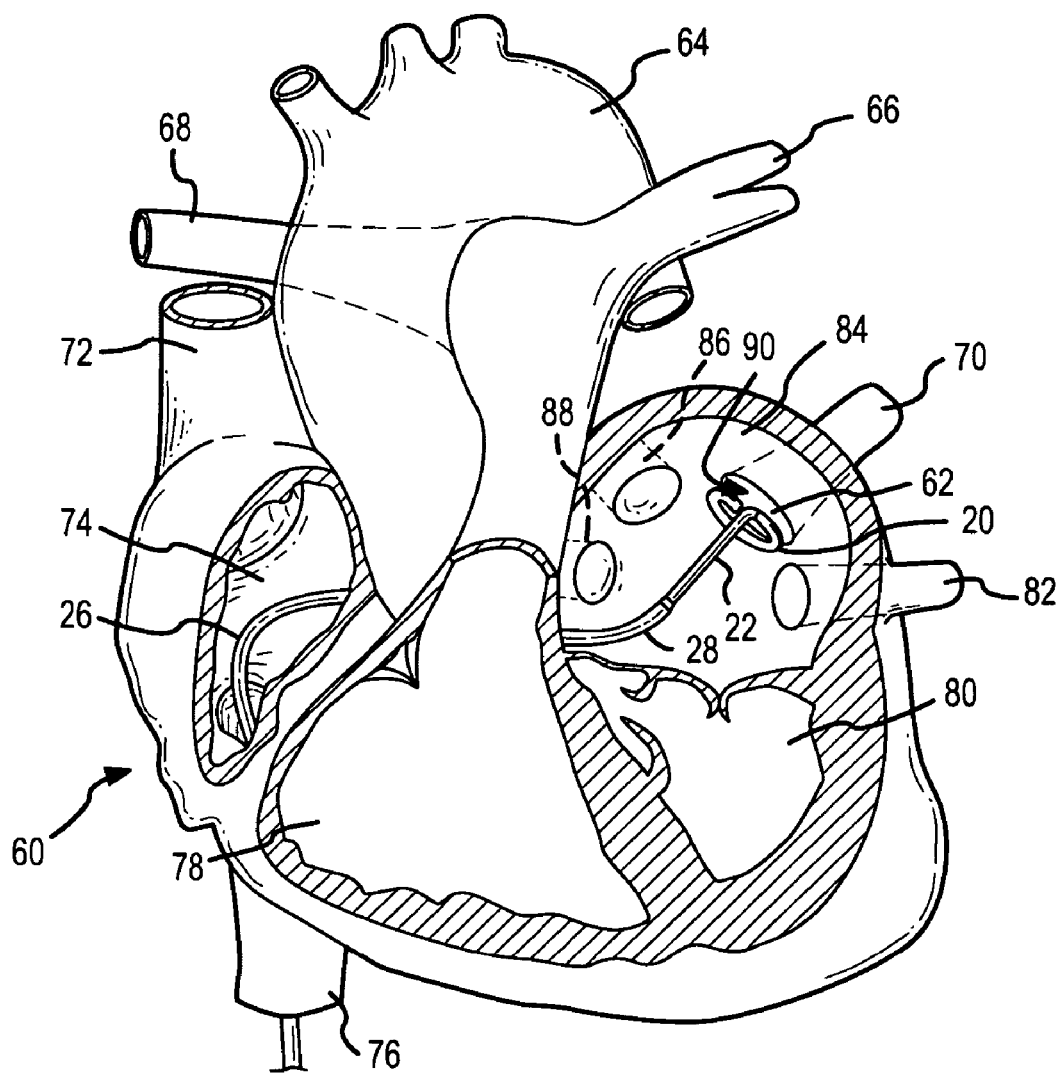
FIG. 19 is an isometric view of a heart with portions of the atria and ventricles broken away to reveal positioning of the catheter depicted in, for example, FIGS. 1, 2, and 16 in the left atrium, adjacent to the left superior pulmonary vein.

As depicted in FIGS. 3 and 4, the catheter 122 may further house a shape-retention wire 148 in order to impart a desired shape to the distal end 12 of the catheter 122 in the area of the ablation electrode section 120. The shape-retention wire 148 is flexible while a clinician negotiates the catheter 122 through the vasculature to reach the heart and enter an atrial chamber. Once the distal end 12 of the catheter 122 reaches the desired cardiac cavity with the ablation electrode section 120, the shape-retention wire 148 assumes a pre-formed shape form, e.g., the C-shaped configuration of the ablation electrode section 120, to accurately orient the ablation electrode section 120 within the cardiac cavity for the procedure to be performed. As shown in FIG. 19 and described later herein, the C-shaped configuration of the ablation electrode section 120 may be used to perform ablation operations at the ostia of vessels entering the atria.

In one embodiment, the shape-retention wire 148 may be NiTinol wire, a nickel-titanium (NiTi) alloy, chosen for its exceptional shape-retention properties. NiTinol wire materials are super elastic—able to sustain a large deformation at a constant temperature—and when the deforming force is released they return to their original, undeformed shape. Thus a catheter 122 incorporating NiTinol shape-retention wire 148 may be inserted into the generally straight lengths of introducer sheaths to reach a desired location and upon emerging from the introducer, the shape-retention wire 148 will assume its "preformed" shape, forming the catheter 122 into the C-shaped curve of the ablation electrode section 120.

Figure 5:
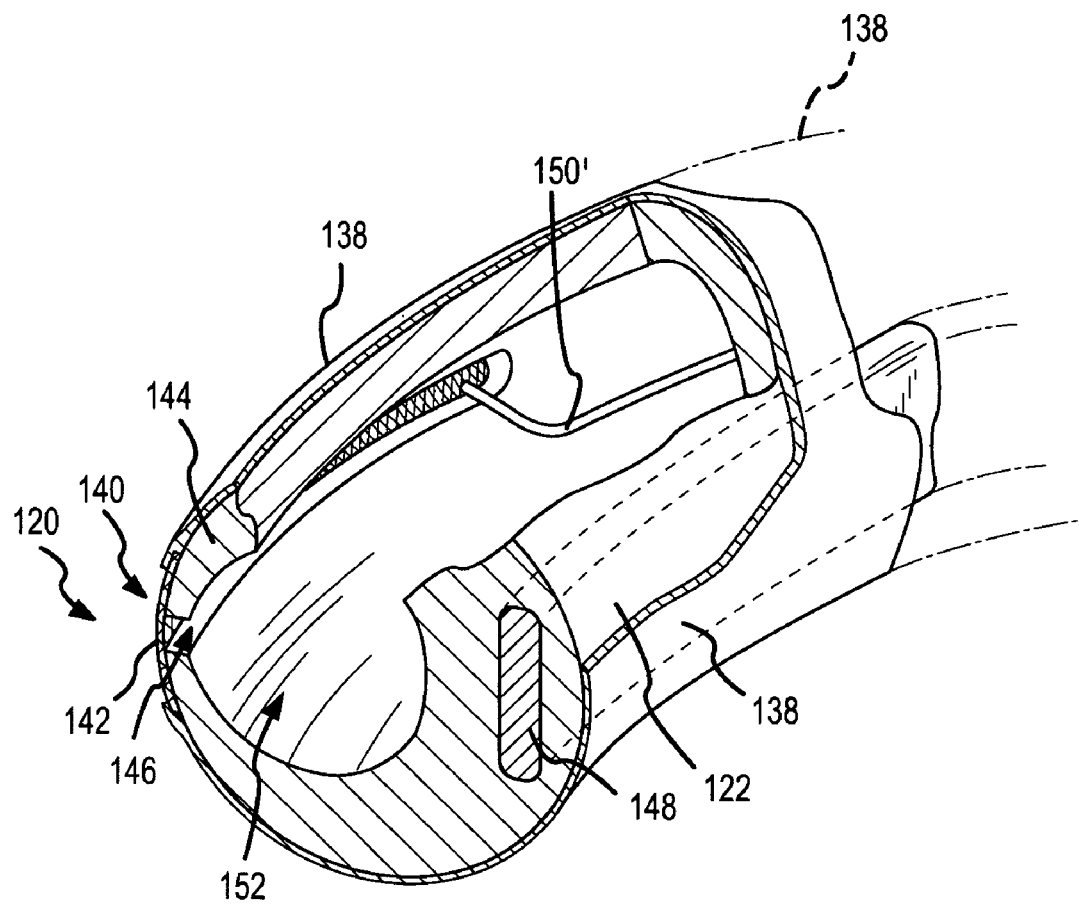
FIG. 5 is an isometric view with a partial cut-away of an alternate embodiment of the catheter of FIG. 2.

An alternate embodiment of the catheter 122 is depicted in FIG. 5. In this embodiment, the electrode 150' is coupled with the mesh material 142, thus transferring RF energy directly to the mesh material 142. In this embodiment instead of the electrode 150' directly energizing the conductive fluid within the fluid lumen 152, the conductive fluid is energized as it passes through the conductive mesh material 142, after passing through the dispersion slot 146. In this embodiment, the energy is more directly transferred to the conductive fluid leaving the ablation electrode 120 portion of the catheter 122 rather than being diluted by the larger volume of conductive fluid within the fluid lumen 152. Further, in the event that the ablation electrode section 120 of the catheter 122 is placed directly against an area of target tissue, the mesh material 142 may be used as a direct ablation electrode. This direct energy transfer from the mesh material 142 to the tissue occurs in addition to the virtual electrode properties of the conductive fluid simultaneously flowing across and being energized by the mesh material 142.

Figure 6:
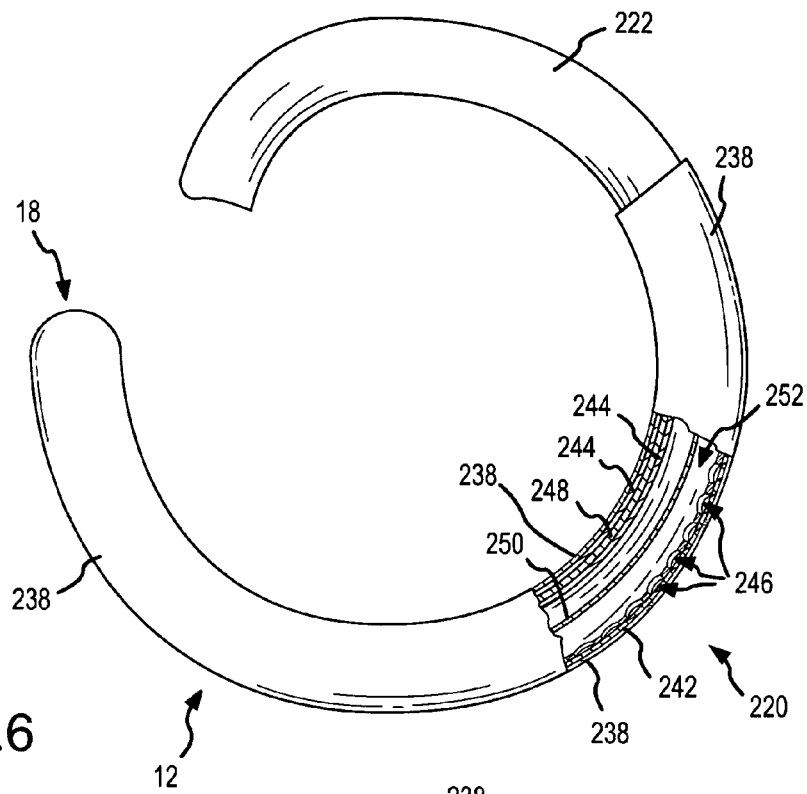
FIG. 6 is a bottom plan view with a partial cut-away of a distal portion of a catheter according to a second embodiment of the present invention.
Figure 7:
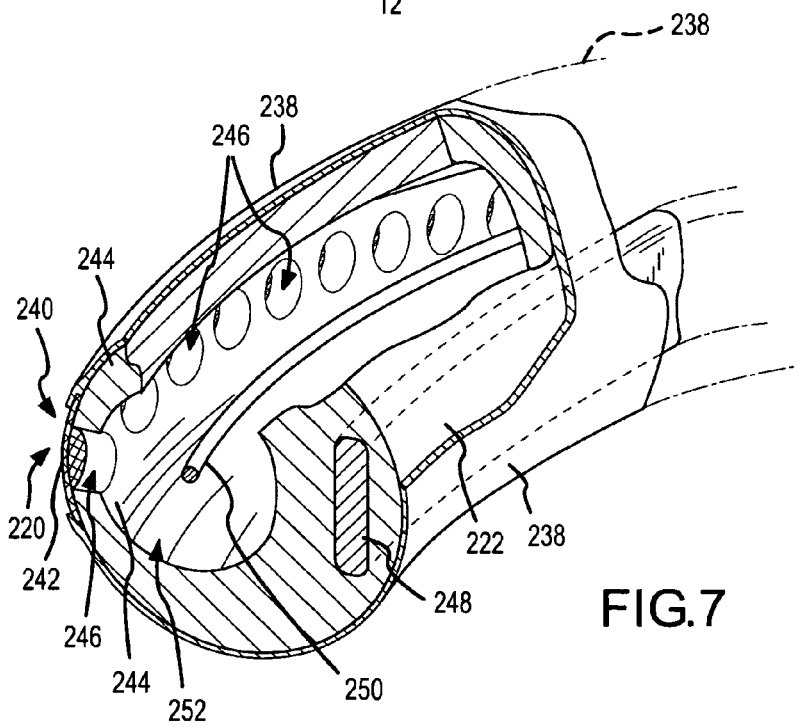
FIG. 7 is an isometric view with a partial cut-away of a portion of the catheter of FIG. 6.

Another embodiment of the invention is depicted in FIGS. 6 and 7. This embodiment is similar to the embodiments of FIGS. 2-5, with the exception that instead of a dispersion slot in the wall of the catheter, a series of dispersion portholes 246 are provided in the catheter wall 244. In other respects, the catheter 222 of this embodiment is generally the same as the embodiments just described. The distal end of the catheter 222 is covered by shrink tubing 238 that extends to the distal tip 18 of the catheter 222. The shrink tubing 238 defines an elongate aperture 240 that extends along the outside wall of the ablation electrode section 220 of the catheter 222 and is positioned over the dispersion portholes 246. Adjacent the catheter wall 244 and covering the dispersion portholes 246 is a mesh material 242. The mesh material 242 is retained against the catheter wall 244 by the shrink tubing 238 as the mesh material 242 extends between the outer surface of the catheter wall 244 and the shrink tubing 238 adjacent the elongate aperture 240.

The catheter 222 again defines a fluid lumen 252 through which conductive fluid is transported to the distal end 12 of the catheter 222. An electrode 250 resides within the fluid lumen 252 and, when energized by a source of RF ablation energy, transfers the RF energy to the conductive fluid within the fluid lumen 252. The conductive fluid within the fluid lumen 252 is forced by fluid pressure through the dispersion portholes 246, through the mesh material 242, and exists the catheter 222 through the elongate aperture 240 in the shrink tubing 238. Again, in this manner the conductive fluid is more evenly distributed as it exists the catheter 222 and thus creates a more uniform lesion in the target tissue. As indicated before, although not shown in this embodiment, the electrode 250 may alternatively be directly attached to the conductive mesh material 242 to directly energize the mesh material 242. This arrangement would still energize the conductive fluid as it passes through the mesh material 242, but after the conductive fluid has already passed through the dispersion portholes 246. A shape-retention/shape-memory wire 248 may additionally reside within the catheter 222 in order to appropriately shape the distal end 12 of the catheter 222.

Figure 8:
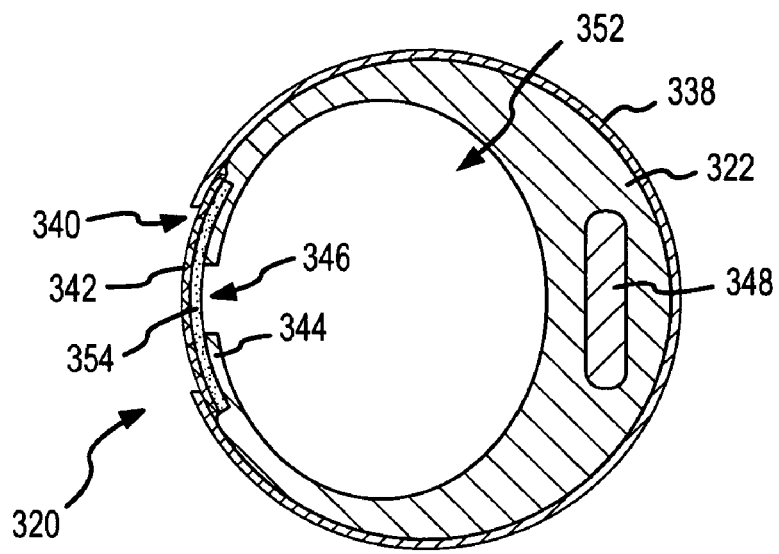
FIG. 8 a cross-section of a catheter according to a third embodiment of the present invention.

Another embodiment of the present invention is depicted in FIG. 8. In this embodiment, the catheter 322 defines a large fluid lumen 352. At the distal end of the catheter 322, an ablation electrode section 320 may be formed by the combination of a dispersion opening 346 within catheter wall 344, a porous layer 354 covering the dispersion opening 346, and a mesh material 342 generally coextensive with and covering the porous layer 354. As in the previous embodiments, the dispersion opening 346 may be either a long slot in the catheter wall 344 or a series of portholes in the catheter wall 344. Further, as in previous embodiments, shrink tubing 338 may be positioned about the distal end of the catheter 322 in order to secure the mesh material 342 and the porous layer 354 over the dispersion opening 346 in the catheter wall 344. Both the mesh material 342 and the porous layer 354 may be thin layers of material and merely rest upon the outer wall of the catheter 322. Alternatively, the catheter wall 344 may be recessed about the dispersion opening 346 allowing the porous layer 354 and the mesh material 322 to lie within the recess with the mesh material 342 being substantially flush with the outer wall of the catheter 322. As before, the shrink tubing 338 defines an elongate aperture 340 exposing the mesh material 342 and allowing fluid under pressure to flow through the dispersion opening 346, porous layer 354, and the mesh material 342. An electrode (not shown) may be either positioned within the fluid lumen 352 to energize conductive fluid or coupled with the mesh material 342 to energize conductive fluid passing through the mesh material 342, thereby creating a virtual electrode. A shape-retention/shape-memory wire 348 may also be provided within the catheter in order to orient the catheter 322 in a desired configuration.

Figure 9:
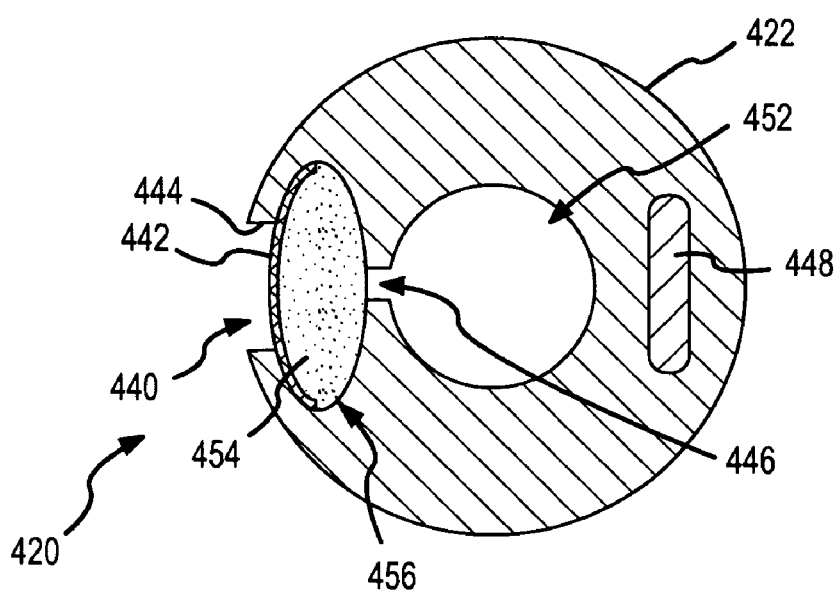
FIG. 9 is a cross-section of a catheter according to a fourth embodiment of the present invention.

A further embodiment of the present invention is depicted in FIG. 9. In this embodiment, the catheter 422 defines a central fluid lumen 452 and further contains a shape-retention/shape-memory wire 448. Additionally, at its distal end, the catheter 422 defines an irrigation cavity 456 that is in fluid communication with the fluid lumen 452 via a dispersion opening 446. As in the previous embodiments, the dispersion opening 446 may be a linear slot or a series of portholes within the catheter wall 444 that allow fluid to flow between the fluid lumen 452 and the irrigation cavity 456. The irrigation cavity 456 is primarily filled with a porous material 454. One side of the irrigation cavity 456 may also be lined with a mesh material 442. An elongate aperture 440 is formed within the catheter wall 444 corresponding to the length of the irrigation cavity 456. The mesh material 442 is interposed between the porous material 454 and the elongate aperture 440. The width of the elongate aperture 440 may be narrower than the corresponding parallel axis of the irrigation cavity 456 to insure that the mesh material 442 and the porous material 454 are retained within the irrigation cavity 456.

The elongate aperture 440 may have a measurable depth between the outer surface of the catheter 422 and surface of the mesh material 442. In such a design, there is a set-off distance between the mesh material 442 and the tissue surface to be ablated. The depth of the elongate aperture 440 formed in the catheter wall 444 acts as a fluid channel to uniformly distribute the conductive fluid as it flows through the porous material 454 and the mesh material 442. By increasing the uniformity of fluid distribution and creating a set-back for the mesh material 442 from the tissue to be ablated, the potential for charring the tissue is greatly reduced. In an alternative embodiment, the mesh material 442 may be positioned adjacent the outer surface of the ablation electrode section 420 of the catheter 422 to provide for actual contact between the mesh material 442 and the tissue to be ablated.

In the embodiments of FIGS. 8 and 9, an additional embodiments to be described further herein, the porous material may be composed of any of a number of micro-porous or macro-porous materials for example, polyvinyl alcohol (PVA), polytetrafluroethylene (PTFE), expanded polytetrafluroethylene (ePTFE), porous polyethylene, and porous polypropylene. In some applications, the porous material may also be composed of collagen. In other embodiments (not depicted herein), the mesh material may be a metal coating on a surface of the porous material, whereby the coated surface of the porous material may also act as the electrode.

The porous material is provided as a buffer to reduce any impact of the pressure drop along the fluid lumen. In some applications, it is desirable to create such greater uniformity in fluid flow. In some instances, because of the pressure drop along the fluid lumen, a non-uniform flow of conductive fluid out of the ablation portion of the catheter causes part of a linear lesion to be under-ablated because of excessive cooling by the fluid while part of the linear lesion is over-ablated and charred because of too little fluid cooling. When porous material is added between the fluid lumen and the exit apertures in the ablation electrode section of the catheter, the pressure drop as the conductive fluid crosses the porous material is much higher than the pressure drop of the fluid in the fluid lumen. Further, the flow rate of conductive fluid exiting the catheter is significantly reduced. By reducing the significance of the pressure drop of the fluid in the fluid lumen and reducing the flow rate, a uniform distribution of fluid flow emerging from the ablation electrode section can be achieved.

Figure 10:
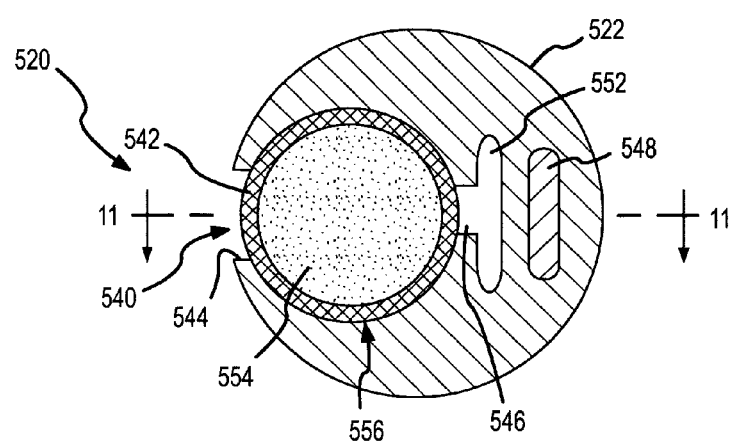
FIG. 10 is a cross-section of a catheter according to a fifth embodiment of the present invention.
Figure 11:
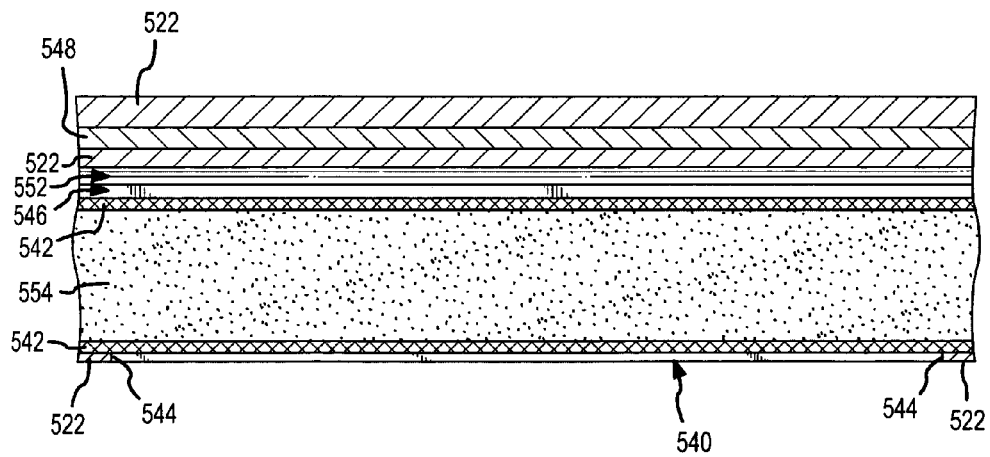
FIG. 11 is a cross-section of the catheter of FIG. 10 along line 11-11 as indicated in FIG. 10.

An additional embodiment of the present invention is depicted in FIGS. 10 and 11. In this embodiment, a catheter 522 again defines a fluid lumen 552 connected to an irrigation cavity 556 via a dispersion channel 546. The catheter 522 may also contain a shape-retention/shape-memory wire 548 to form the catheter 522 into a desired configuration. As before, the irrigation cavity 556 extends within an ablation electrode section 520 of the distal end 12 of the catheter 522. In this embodiment, the dispersion channel 546 is generally coextensive with the length of the irrigation cavity 556. The irrigation cavity 556 houses an outer mesh tube 542 which further surrounds a column of porous material 554. In this embodiment, use of polyvinyl alcohol as the porous material 554 may be desirable. An elongate opening 540 is formed in the catheter wall 544 on an opposite side of the irrigation cavity 556 from the dispersion channel 546. The elongate aperture 540 is generally coextensive with the length of the irrigation cavity 556 and exposes an adjacent portion of the mesh tube 542. In this embodiment, the mesh tube 542 is generally energized as an electrode. Conductive fluid flows from the fluid lumen 552 through the dispersion channel 546, through the adjacent wall of the mesh tube 542, through porous material 554, and then exits the irrigation cavity 556, again passing through the mesh tube 542 to exit the elongate aperture 540 in the catheter wall 544.

Figure 12:
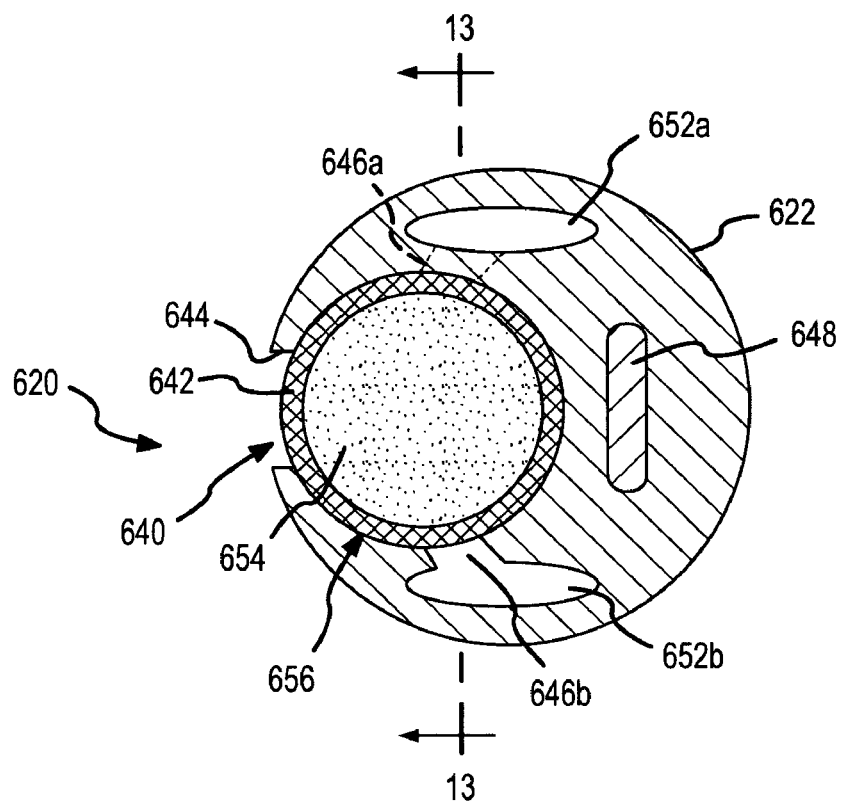
FIG. 12 is a cross-section of a catheter according to a sixth embodiment of the present invention.
Figure 13:
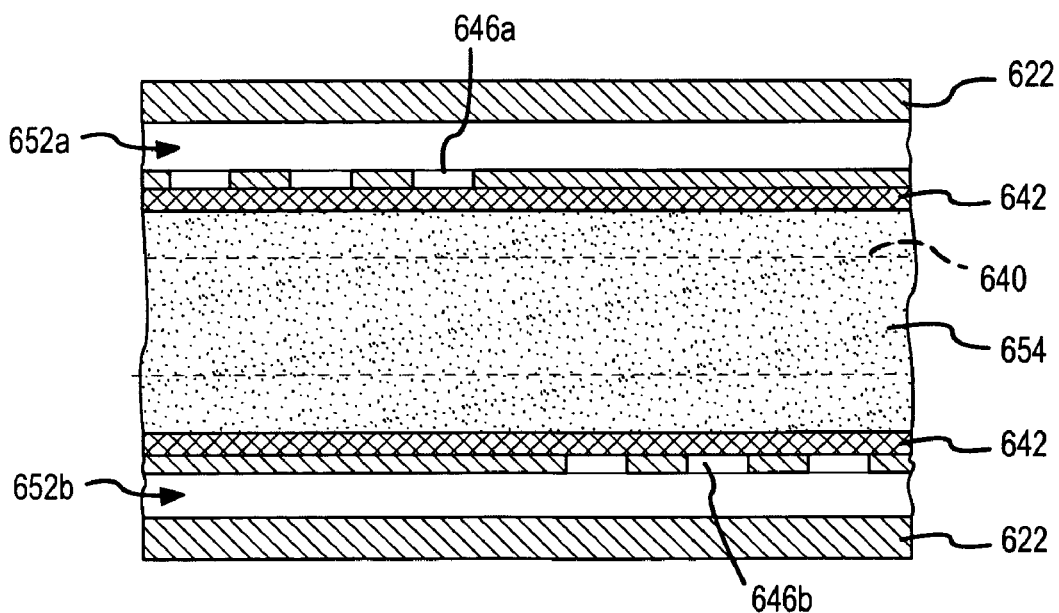
FIG. 13 is a cross-section of the catheter of FIG. 12 along line 13-13 as indicated in FIG. 12.

An alternative to the embodiment of FIGS. 10 and 11 is presented in FIGS. 12 and 13. In this embodiment, two fluid lumens are provided within the catheter 622. A first fluid lumen 652a is connected with a first section of the irrigation cavity 656 by a first set of dispersion portholes 646a. Similarly, the second fluid lumen 652b is connected with a second section of the irrigation cavity 656 by a second set of dispersion portholes 646b. In this design, the first fluid lumen 652a primarily irrigates only first portion of the irrigation cavity 656 while the second fluid lumen irrigates a second portion of the irrigation cavity 656. While the dispersion portholes 646a, 646b are depicted in this embodiment as structures for fluid communication between the first fluid lumen 652a and the second fluid lumen 652b and the irrigation cavity 656, it should be recognized that a single channel, multiple channels, or other configurations of dispersion openings may be used to provide the desired fluid communication. As in the previous embodiment, the irrigation cavity 656 in FIGS. 12 and 13 is lined with a mesh tube 642 that further surrounds a porous material 654. In this embodiment, use of polyvinyl alcohol as the porous material 654 may be desirable. An elongate aperture 640 in the catheter wall 644 exposes a surface of the mesh tube 642 and allows for the conductive fluid to flow out of the ablation section of the catheter 622. Again, the catheter may also house a shape-retention/shape-memory wire 648 in order to impart desired shape to catheter 622.

Figure 14:
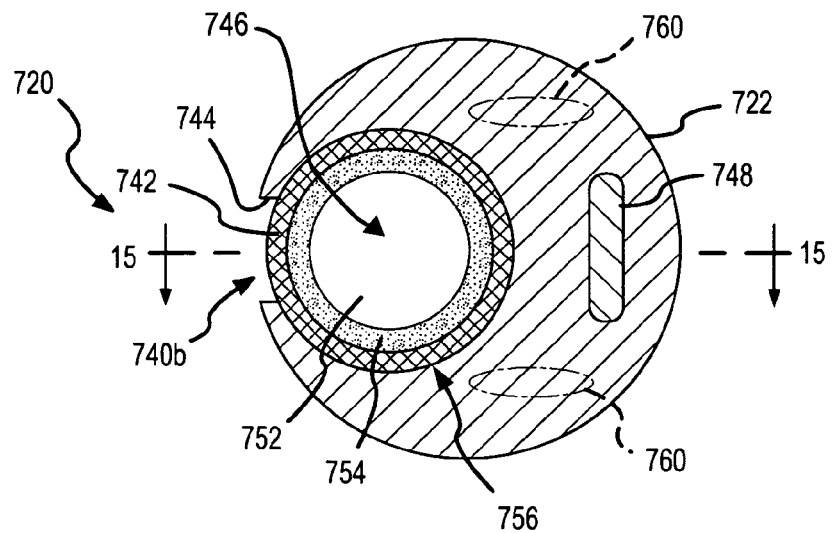
FIG. 14 is a cross-section of a catheter according to a seventh embodiment of the present invention.
Figure 15:
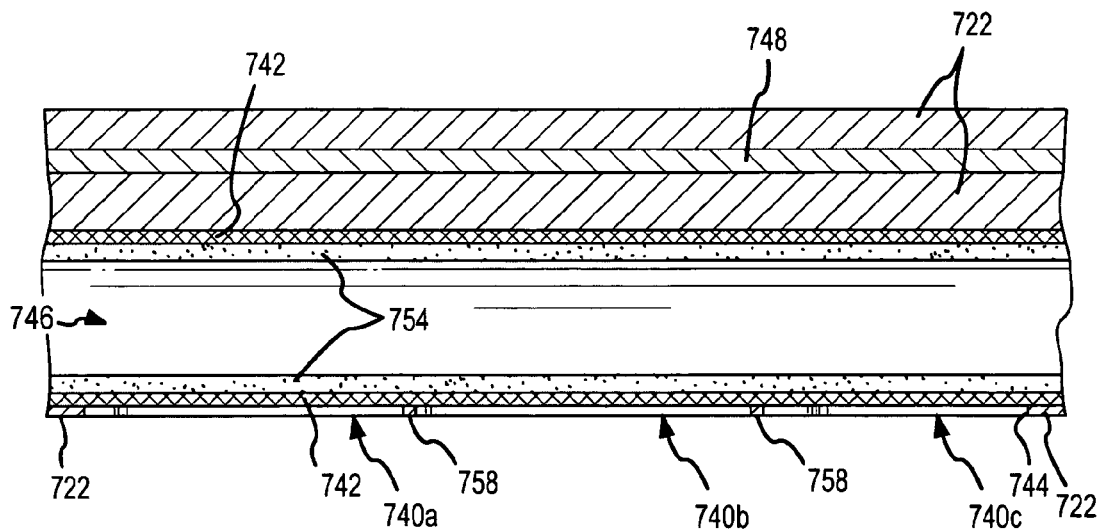
FIG. 15 is a cross-section of the catheter of FIG. 14 along line 15-15 as indicated in FIG. 14.

An additional embodiment of the present invention is depicted in FIGS. 14 and 15. In this embodiment, the catheter 722 defines a fluid lumen 752 that transitions to an irrigation cavity 756 within a distal end 12 of the catheter 722. A mesh tube 742 lines the interior wall of the irrigation cavity 756. Positioned within the mesh tube 742 is a second tube of porous material 754. The outer diameter of the porous material tube 754 is generally the same as of slightly smaller than the inner diameter of the mesh tube 742 such that the mesh tube 742 and the porous material tube 754 fit snugly together. In this embodiment, use of expanded polytetrafluroethylene as the porous material tube 754 may be desirable. The interior lumen of the tube of porous material further defines the dispersion opening 746, transferring fluid from the fluid lumen 752 to the porous material 754 and the mesh material 742. In other words, with respect to the dispersion opening being considered as an opening in the catheter as in previous embodiments, the fluid lumen 752 of the catheter 722 in the present embodiment also functions as the dispersion opening 746 in the portion of the catheter 722 identified as the irrigation cavity 756.

In this embodiment, a series of elongate apertures 740a, 740b, 740c, separated by aperture bridges 758, are defined within the catheter wall 744. It may be desirable to section an elongate aperture within the catheter wall 744 with aperture bridges 758 in order to provide additional stability to the catheter 722 over the length of an extensive opening in the catheter wall 744. As in previous embodiments, the elongate apertures 740a, 740b, 740c expose a surface of the mesh tube 742 and allow for the exit of conductive fluid from the ablation section 720 of the catheter 722. Also, as in previous embodiments, a shape-retention/shape-memory wire 748 may be provided within the catheter 722 to appropriately shape the catheter 722. Additionally, because in this design the fluid lumen 752 is coaxial with the irrigation cavity 756, there may be additional room within the catheter 722 to provide alternate lumens 760, for example, for the provision of steering cables or sensing leads.

Figure 16:
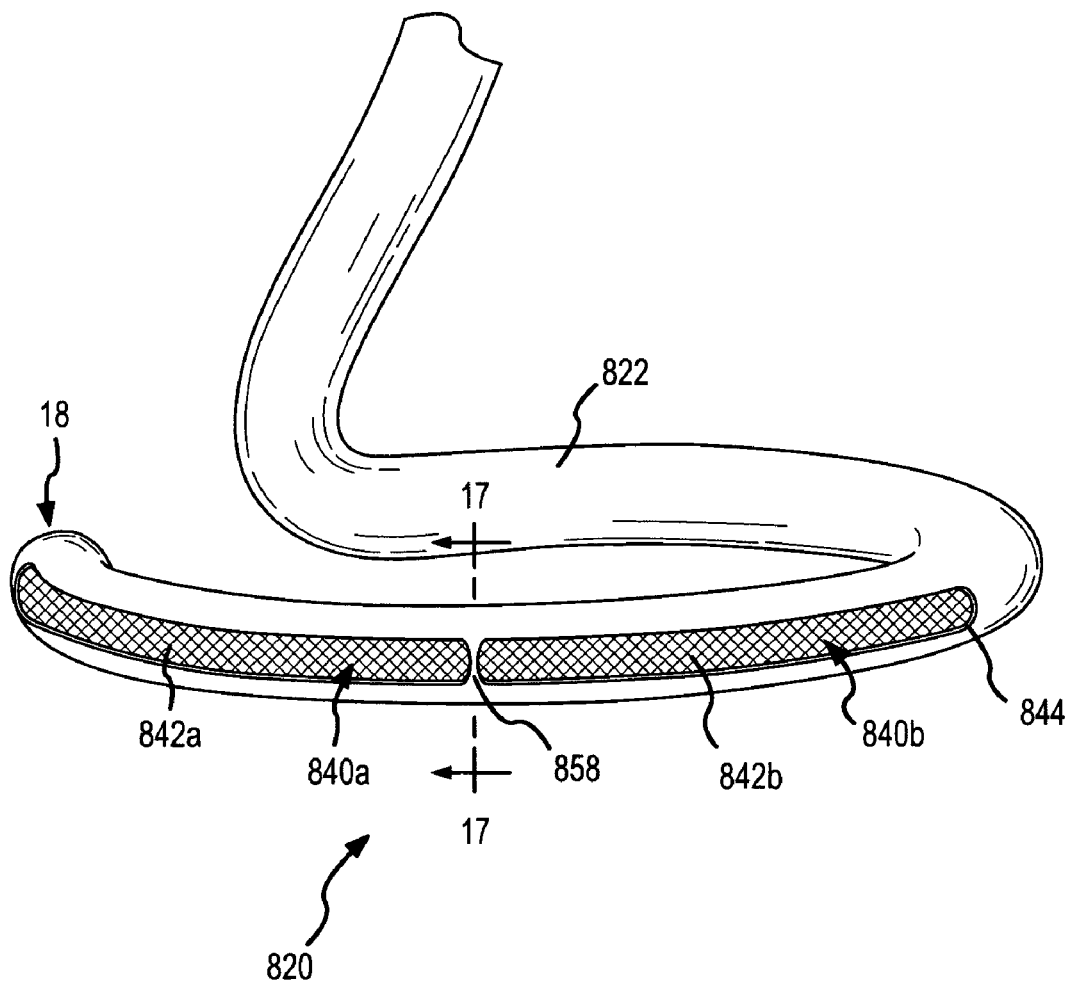
FIG. 16 is an isometric view of a distal portion of a catheter, including an ablation tip, according to an eighth embodiment of the present invention.
Figure 17:
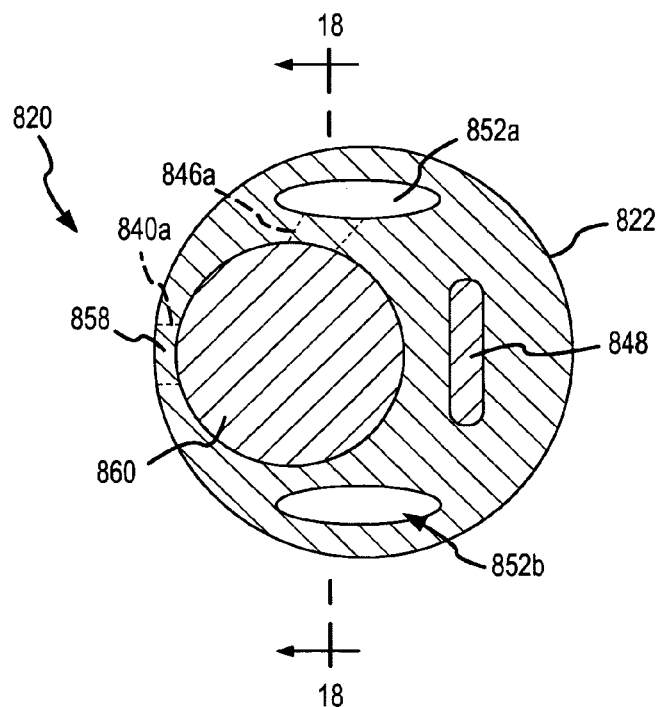
FIG. 17 is a cross-section of the catheter of FIG. 16 along line 17-17 as indicated in FIG. 16.
Figure 18:
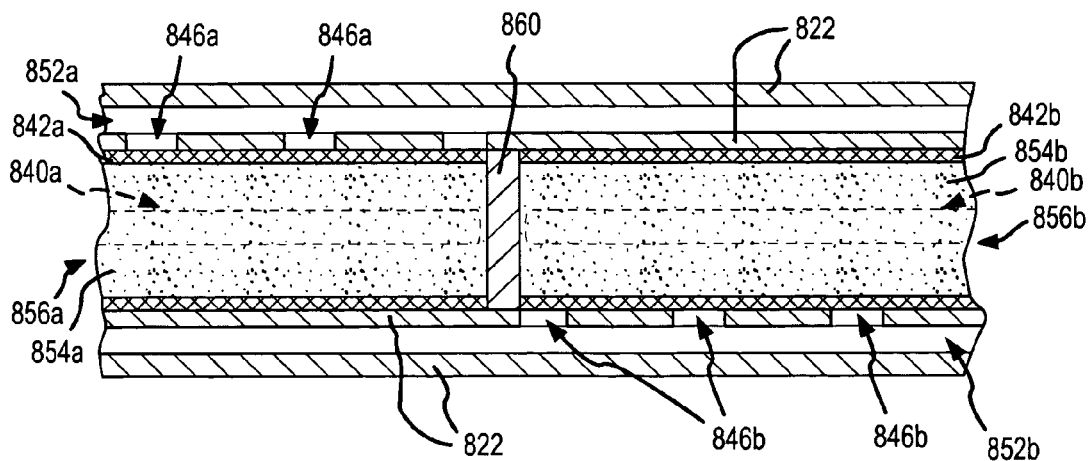
FIG. 18 is a cross-section of the catheter of FIG. 16 along line 18-18 as indicated in FIG. 17.

An alternate embodiment of the invention is depicted in FIGS. 16-18. In this embodiment, similar to the previous embodiment, the catheter 822 has a pair of elongate apertures within the catheter wall. A first elongate aperture 840a is separated from a second elongate aperture 840b by an aperture bridge 858. The catheter 822 further defines a first fluid lumen 852a and a second fluid lumen 852b, which each transport a conductive fluid to the distal end 12 of the catheter 822. The distal end 12 of the catheter 822 also houses a first irrigation cavity 856a and a second irrigation cavity 856b. The first and second irrigation cavities 856a, 856b are separated by a plug 860. The plug 860 is nonporous and is an insulating dielectric, thereby both electrically isolating the first irrigation cavity 856a from the second irrigation cavity 856b as well as physically preventing fluid flow between the first and second irrigation cavities 856a and 856b.

Similar to the embodiment of FIGS. 12 and 13, the present embodiment depicted in FIGS. 16-18 supplies fluid to the first irrigation cavity 856a through the first fluid lumen 852a while separately providing fluid to the second irrigation cavity 856b through the second fluid lumen 852b. The first fluid lumen 852a is in fluid communication with the first irrigation cavity 856a through a first series of dispersion portholes 846a. Likewise, the second fluid lumen 852b is in fluid communication with the second irrigation cavity 856b through a second series of dispersion portholes 846b. Each of the first and second irrigation cavities 856a, 856b is lined with a separate conductive mesh tube 842a and 842b, respectively. A separate electrode lead (not shown) is attached to each of the first and second conductive mesh tubes 842a, 842b to deliver RF energy from an energy source connected with the proximal end of the catheter. Each of the first and second conductive mesh tubes 842a, 842b is further filled with a porous material 854a, 854b. The first and second elongate apertures 840a, 840b expose coextensive portions of the surfaces of the mesh tubes 842a, 842b. It should be noted that as in previous embodiments, a shape-retention/shape-memory wire 848 may be provided within catheter 822 to impart a desired configuration to the catheter 822.

The design of the ablation electrode section 820 of the catheter 822 allows for a first half of the ablation electrode section 820 to be energized for an initial period and then to separately energize the second half of the ablation electrode section 820 for a second period. It may be desirable to perform an ablation procedure in successive steps in a circumstance where the length of the desired lesion demands more power than potentially available from the source of RF ablation energy. The present design allows energy to be delivered to two or more sections of the ablation electrode 820 successively and sequentially. This embodiment further provides the option of delivering the conductive fluid to the first and second irrigation cavities 856a, 856b in the ablation electrode section 820 either continuously or successively and sequentially in combination with the delivery of the RF energy. If the aperture bridge 858 and plug 860 between the electrodes are sufficiently narrow, a single, uninterrupted lesion may be formed in the target tissue.

In one experiment, a catheter with an ablation section of the embodiment depicted in FIGS. 16-18 was constructed with first and second elongate apertures within the catheter wall, each 33 mm long with a separation distance of 0.030 in. A saline source was connected to the both the first fluid lumen and the second fluid lumen of the catheter at a flow rate of 36 ml/min. The first conductive mesh tube was energized with 30 watts of power of RF energy for a period of 60 seconds. After an interval of 15 seconds, the second conductive mesh tube was energized with 30 watts of power for a second period of 60 seconds. The resulting lesion in the tissue was continuous measuring 77 mm in length with and average depth of 2.7 mm.

FIG. 19 schematically depicts the catheter 22 and ablation electrode section 20 according to a generic embodiment of the present invention being used to ablate tissue in a left superior pulmonary vein 70. FIG. 19 includes a number of primary components of the heart 60 to orient the reader. In particular, starting in the upper left-hand portion of FIG. 19, and working around the periphery of the heart 60 in a counterclockwise fashion, the following parts of the heart 60 are depicted: the superior vena cava 72, the right atrium 74, the inferior vena cava 76, the right ventricle 78, the left ventricle 80, the left inferior pulmonary vein 82, left superior pulmonary vein 70, the left atrium 84, the right superior pulmonary vein 86, the right inferior pulmonary vein 88, the left pulmonary artery 66, the arch of the aorta 64, and the right pulmonary artery 68.

The distal end of the ablation electrode section 20 is positioned adjacent to the ostium 90 of the left superior pulmonary vein 70 using known procedures. For example, to place the ablation electrode section 20 in the position shown in FIG. 19, the right venous system may be first accessed using the "Seldinger technique." In this technique, a peripheral vein (such as a femoral vein) is first punctured with a needle and the puncture wound is dilated with a dilator to a size sufficient to accommodate an introducer (e.g., the outer guiding introducer 26 shown in FIG. 1). The outer guiding introducer 26 with at least one hemostatic valve (see FIG. 1) is seated within the dilated puncture wound while maintaining relative hemostasis. From there, the outer guiding introducer 26 is advanced along the peripheral vein, into the inferior vena cava 76, and into the right atrium 74. A transeptal sheath may be further advanced through the outer guiding introducer 26 to create a hole in the interatrial septum between the right atrium 74 and the left atrium 84. Once the outer guiding introducer 26 is in place in the right atrium 74, the inner guiding introducer 28, housing the catheter 22 with the ablation electrodesection 20 on the distal end, is introduced through the hemostatic valve 6 of the outer guiding introducer 26 and navigated into the right atrium 74, through the hole in the interatrial septum, and into the left atrium 84. Once the inner guiding introducer 28 is in the left atrium 84, the ablation electrode section 20 of the catheter 22 and may be advanced through the distal tip of the inner guiding introducer 28. The ablation electrode section 20 as shown in FIG. 19 is being inserted into the ostium 90 of the left superior pulmonary vein 70 to contact the tissue of the walls of the vein. The configuration of the ablation electrode section 20 as depicted in FIG. 2 is advantageous for maintaining consistent contact with tissue in a generally cylindrical vessel. Other configurations of the ablation electrode section 20 may be used to greater advantage on tissue surfaces of other shapes.

While the ablation electrode 20 is in the left superior pulmonary vein 70, the ablation electrode section 20 may be energized to create the desired lesion in the left superior pulmonary vein 70. The RF energy emanating from the ablation electrode section 20 is transmitted through the conductive fluid medium, which flows through the fluid lumen, through the dispersion openings, through the porous material (depending upon the particular embodiment), through the mesh layer, and impacts the adjacent tissue. Thus, a lesion is formed in the tissue by the RF energy.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A catheter with a distal ablation electrode section, the catheter comprising:
a proximal section;
an ablation section at a distal end of the catheter;
a catheter wall defining at least one fluid lumen extending from the proximal section to the ablation section;
an electrode lead positioned within the at least one fluid lumen extending within the ablation section;
at least one dispersion opening within the catheter wall in the ablation section oriented longitudinally along a length of the ablation section, wherein the at least one dispersion opening is in fluid communication with the at least one fluid lumen;
a porous layer covering the at least one dispersion opening; and
a length of mesh material generally coextensive with and positioned adjacent to the at least one dispersion opening on the opposing side of the at least one dispersion opening from the at least one fluid lumen, the mesh material also configured as an electrode, and the mesh material covering the porous layer and configured to allow fluid under pressure to flow through the at least one dispersion opening;
wherein the porous layer is interposed both between the mesh material and the at least one dispersion opening and between the mesh material and the outer surface of the catheter adjacent the at least one dispersion opening.

2. The catheter of claim 1, wherein the mesh material is a conductive material.

3. The catheter of claim 2, wherein the mesh material is selected from a group of materials consisting of: platinum, platinum/iridium, gold, stainless steel, and carbon fiber.

4. The catheter of claim 1, wherein the porous layer is selected from a group of materials consisting of: a microporous material, a macro-porous material, polyvinyl alcohol (PVA), polytetrafluroethylene (PTFE), expanded polytetrafluroethylene (ePTFE), porous polyethylene, porous polypropylene, and collagen.

5. The catheter of claim 1, wherein the at least one dispersion opening comprises a plurality of portholes arranged linearly and oriented longitudinally along the length of the ablation section of the catheter.

6. The catheter of claim 1, wherein the dispersion opening comprises at least one linear slot oriented longitudinally along a length of the ablation section of the catheter.

7. The catheter of claim 1, wherein the mesh material comprises a first mesh section and a second mesh section and the first mesh section is electrically insulated from the second mesh section.

8. A method of creating a uniform flow of a fluid emanating from an ablation section at a distal end of a catheter, the method comprising
flowing a conductive fluid through a lumen in the catheter, wherein a first pressure drop across the conductive fluid in the lumen is created between a proximal end of the catheter and the ablation section;
flowing the conductive fluid from the lumen through a porous material positioned in the ablation section;
wherein a second pressure drop is created between a first surface of the porous material and a second surface of the porous material; and
wherein the second pressure drop through the porous material is higher than the first pressure drop; and
flowing the conductive fluid through a mesh electrode covering the porous material, the mesh electrode configured as both the only electrode and the only mesh material covering the porous material, the mesh electrode also securing the porous material on the catheter during flowing of the conductive fluid.

9. A catheter with a distal ablation electrode section, the catheter comprising:
a proximal section;
an ablation section at a distal end of the catheter;
a catheter wall defining at least one fluid lumen extending from the proximal section to the ablation section;
an electrode lead positioned within the at least one fluid lumen extending within the ablation section;
at least one dispersion opening within the catheter wall in the ablation section oriented longitudinally along a length of the ablation section, wherein the at least one dispersion opening is in fluid communication with the at least one fluid lumen; a porous layer covering the at least one dispersion opening;
a length of mesh material generally coextensive with and positioned adjacent to the at least one dispersion opening on the opposing side of the at least one dispersion opening from the at least one fluid lumen, the mesh material covering the porous layer and configured to allow fluid under pressure to flow through the at least one dispersion opening; and
a retention layer about the distal end of the catheter;
wherein the retention layer defines an elongate aperture generally coextensive with the dispersion opening; and
wherein a perimeter edge of the mesh material is retained between the retention layer adjacent the elongate aperture and an outer surface of the catheter adjacent the at least one dispersion opening.

10. The catheter of claim 9, wherein the retention layer is an insulating shrink wrap tube.

11. A catheter with a distal ablation electrode section, the catheter comprising:
a proximal section;
an ablation section at a distal end of the catheter;
a catheter wall defining at least one fluid lumen extending from the proximal section to the ablation section;
an electrode lead positioned within the at least one fluid lumen extending within the ablation section;
at least one dispersion opening within the catheter wall in the ablation section oriented longitudinally along a length of the ablation section, wherein the at least one dispersion opening is in fluid communication with the at least one fluid lumen; a porous layer covering the at least one dispersion opening;
a length of mesh material generally coextensive with and positioned adjacent to the at least one dispersion opening on the opposing side of the at least one dispersion opening from the at least one fluid lumen, the mesh material covering the porous layer and configured to allow fluid under pressure to flow through the at least one dispersion opening; and
wherein the porous layer is interposed both between the mesh material and the at least one dispersion opening and between the mesh material and the outer surface of the catheter adjacent the at least one dispersion opening.

12. The catheter of claim 11, wherein the porous layer is selected from a group of materials consisting of: a microporous material, a macro-porous material, polyvinyl alcohol (PVA), polytetrafluoroethylene (PTFE), expanded polytetrafluroethylene (ePTFE), porous polyethylene, porous polypropylene, and collagen.

13. A catheter with a distal ablation electrode section, the catheter comprising:
a proximal section;

an ablation section at a distal end of the catheter;
a catheter wall defining at least one fluid lumen extending from the proximal section to the ablation section;
an electrode lead positioned within the at least one fluid lumen extending within the ablation section;
at least one dispersion opening within the catheter wall in the ablation section oriented longitudinally along a length of the ablation section, wherein the at least one dispersion opening is in fluid communication with the at least one fluid lumen;
a porous layer covering the at least one dispersion opening;
a length of mesh material generally coextensive with and positioned adjacent to the at least one dispersion opening on the opposing side of the at least one dispersion opening from the at least one fluid lumen, the mesh material also configured as an electrode, and the mesh material covering the porous layer and configured to allow fluid under pressure to flow through the at least one dispersion opening;
wherein the porous layer is interposed both between the mesh material and the at least one dispersion opening and between the mesh material and the outer surface of the catheter adjacent the at least one dispersion opening;
a retention layer about the distal end of the catheter;
wherein the retention layer defines an elongate aperture generally coextensive with the dispersion opening; and
wherein a perimeter edge of the mesh material is retained between the retention layer adjacent the elongate aperture and an outer surface of the catheter adjacent the at least one dispersion opening.

14. The catheter of claim 13, wherein the retention layer is an insulating shrink wrap tube.

15. The catheter of claim 13, wherein the mesh material is a conductive material.

16. The catheter of claim 15, wherein the mesh material is selected from a group of materials consisting of: platinum, platinum/iridium, gold, stainless steel, and carbon fiber.

17. The catheter of claim 13, wherein the porous layer is selected from a group of materials consisting of: a micro-porous material, a macro-porous material, polyvinyl alcohol (PVA), polytetrafluoroethylene (PTFE), expanded polytetrafluroethylene (ePTFE), porous polyethylene, porous polypropylene, and collagen.

18. The catheter of claim 13, wherein the at least one dispersion opening comprises a plurality of portholes arranged linearly and oriented longitudinally along the length of the ablation section of the catheter.

19. The catheter of claim 13, wherein the dispersion opening comprises at least one linear slot oriented longitudinally along a length of the ablation section of the catheter.

20. The catheter of claim 13, wherein the mesh material comprises a first mesh section and a second mesh section and the first mesh section is electrically insulated from the second mesh section.

* * * * *